United States Patent
Mande et al.

(10) Patent No.: US 9,070,226 B2
(45) Date of Patent: Jun. 30, 2015

(54) IDENTIFICATION OF MARKER FEATURES IN MULTI-DIMENSIONAL DATA

(71) Applicant: TATA CONSULTANCY SERVICES LIMITED, Maharashtra (IN)

(72) Inventors: Sharmila S. Mande, Pune (IN); Kuntal Kumar Bhusan, Pune (IN); Tarini Shankar Ghosh, Pune (IN)

(73) Assignee: TATA CONSULTANCY SERVICES, Mumbai (IN)

( * ) Notice: Subject to any disclaimer, the term of this patent is extended or adjusted under 35 U.S.C. 154(b) by 234 days.

(21) Appl. No.: 13/778,799

(22) Filed: Feb. 27, 2013

(65) Prior Publication Data

US 2013/0328880 A1    Dec. 12, 2013

(30) Foreign Application Priority Data

Jun. 12, 2012  (IN) .......................... 1713/MUM/2012

(51) Int. Cl.
| | |
|---|---|
| *G06T 11/20* | (2006.01) |
| *G06K 9/00* | (2006.01) |
| *G06K 9/62* | (2006.01) |
| *G06F 19/26* | (2011.01) |
| *G06F 19/24* | (2011.01) |

(52) U.S. Cl.
CPC ............ *G06T 11/206* (2013.01); *G06K 9/0014* (2013.01); *G06K 9/6222* (2013.01); *G06F 19/26* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 2006/0064415 A1* | 3/2006 | Guyon et al. ...................... 707/6 |
| 2007/0280530 A1* | 12/2007 | Fung et al. .................... 382/159 |
| 2011/0097001 A1* | 4/2011 | Labbi et al. ................... 382/225 |
| 2014/0037172 A1* | 2/2014 | Madabhushi et al. ........ 382/131 |

OTHER PUBLICATIONS

Ankerst, et al., "Similarity clustering of dimensions for an enhanced visualization of multidimensional data", Proceedings of IEEE Symposium on Information Visualization (InfoVis), Oct. 19, 1998, pp. 52-60, and 153.
Kwasnicka, et al., "Visualization as a method for relationship discovery in data", Proceedings of Polish Information Processing Society Conference (PIPS), 2005, pp. 153-157.
Tatu, et al., "Automated Analytical Methods to Support Visual Exploration of High-Dimensional Data", IEEE Transactions on Visualization and Computer Graphics, vol. 17, No. 5, May 2011, pp. 584-597.
* cited by examiner

*Primary Examiner* — Kee M Tung
*Assistant Examiner* — Xin Sheng
(74) *Attorney, Agent, or Firm* — Lee & Hayes, PLLC

(57) ABSTRACT

Method(s) and system(s) for identifying marker features of various subsets of a multi-dimensional data are provided. Each subset includes various data points associated with various features. Each of the data points are defined by feature values corresponding to the associated features. The method includes identifying feature pairs based on a matrix of the data points and the features, and computing correlation distances between features in each of the feature pairs. The method includes generating a non-linear pattern of the plurality of features in a two-dimensional plane. Additionally, the method includes calculating a threshold feature value for the associated features of the data points of a particular subset and representing the threshold feature value as a threshold non-linear pattern in the two-dimensional plane. The method includes determining the marker features based on a relative position of the features with respect to the threshold feature value in the two-dimensional plane.

14 Claims, 16 Drawing Sheets

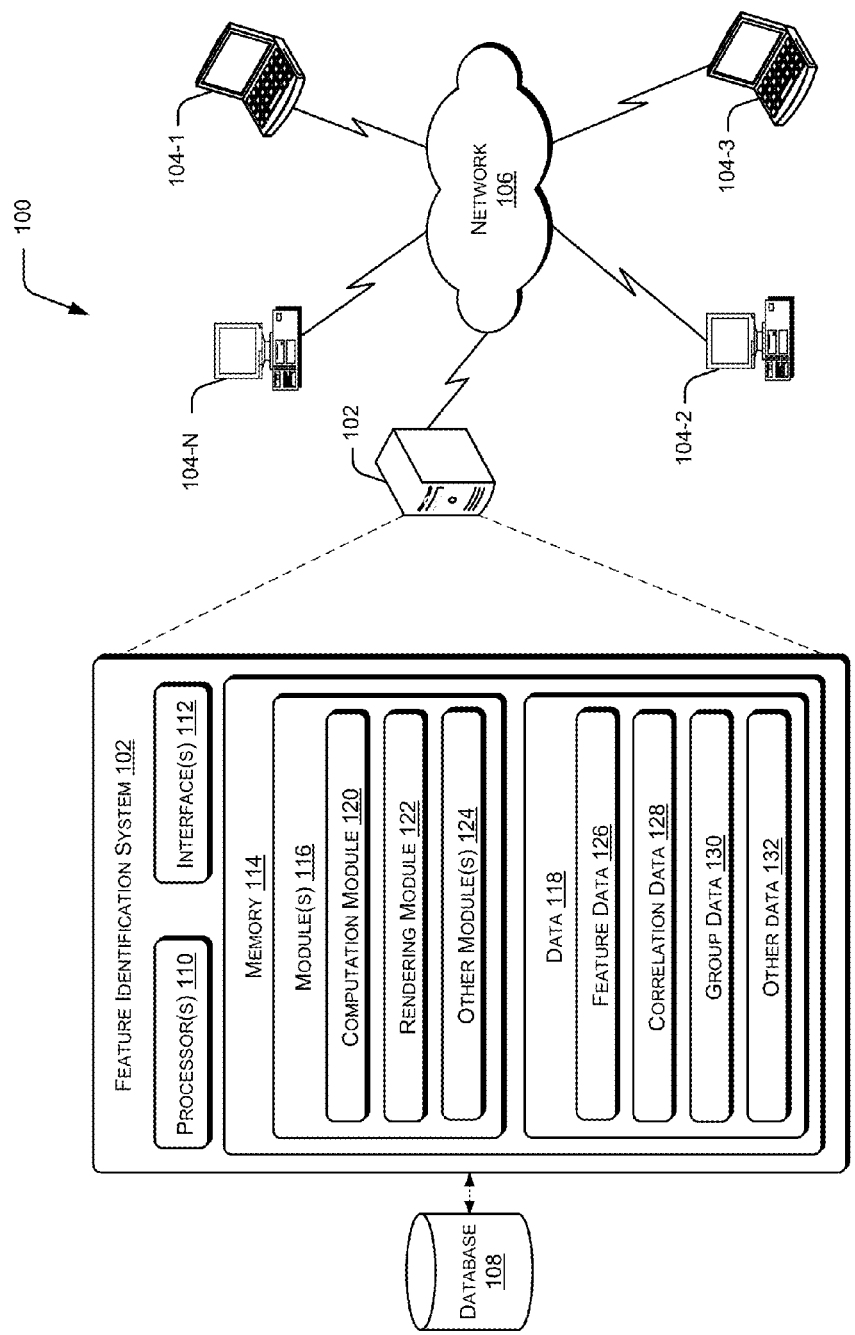

IDENTIFICATION OF MARKER FEATURES IN MULTI-DIMENSIONAL DATA

TECHNICAL FIELD

The present subject matter relates, in general, to multi-dimensional data, and in particular, to identification of marker features in the multi-dimensional data.

BACKGROUND

Rendering data using different visual data mining techniques for enhanced visualization is an emerging trend used to display, analyze, and explore multi-dimensional data, such as scientific data. Visualization of the multi-dimensional data may be defined as use of computer-supported, interactive, visual representations of the multi-dimensional data in order to amplify cognition. Presently, various visual data mining tools and visualization techniques exist for graphically rendering the multi-dimensional data.

Typically, when rendering the multi-dimensional data with a large number of features, the visual data mining tools graphically represent the multi-dimensional data into a lesser dimensional space after applying an automated data mining algorithm or technique. This may result in completely ignoring the contribution of individual features of the multi-dimensional data or decomposition of the information pertaining to the individual features.

SUMMARY

This summary is provided to introduce concepts related to identification of marker features in the multi-dimensional data, which are further described below in the detailed description. This summary is neither intended to identify essential features of the claimed subject matter nor is it intended for use in determining or limiting the scope of the claimed subject matter.

In an embodiment, method(s) and system(s) for identifying marker features of one or more subsets of a multi-dimensional data. Each subset may include a plurality of data points associated with a plurality of features. Further, each of the plurality of data points may be defined by feature values corresponding to the associated features. The method may include identifying a plurality of feature pairs based on a matrix of the plurality of data points and the plurality of features. The method may also include computing correlation distances between features in each of the plurality of feature pairs, such that a lower correlation distance between the features may indicate a highly related feature pair. Furthermore, the method may include generating a non-linear pattern of the plurality of features in a two-dimensional plane. The non-linear pattern may be based on the correlation distances, such that the features in the highly related feature pair may be placed closer to each other than the features not highly related to each other.

Additionally, the method may include calculating a threshold feature value for the associated features of the data points of a particular subset from amongst the one or more subsets. The method may further include representing the threshold feature value as a threshold non-linear pattern in the two-dimensional plane. Thereafter, the features of the data points in the particular subset may be positioned with respect to the threshold feature value in the two-dimensional plane. Moreover, the method may include determining the marker features based on a relative position of the features with respect to the threshold feature value in the two-dimensional plane.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components.

FIG. 1 illustrates a network environment implementation of an identification system, in accordance with an embodiment of the present subject matter.

DETAILED DESCRIPTION

Figure 1A:
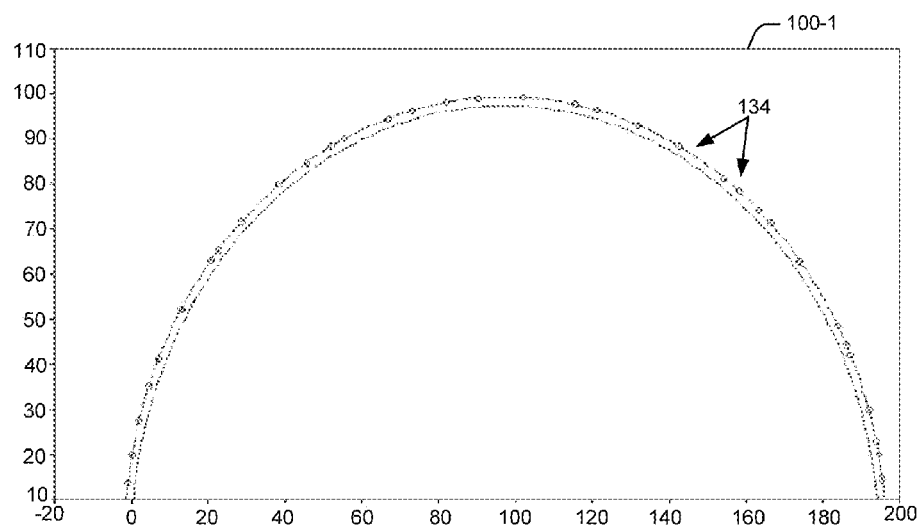
FIG. 1a illustrates a non-linear pattern in a two-dimensional plane, in accordance with an embodiment of the present subject matter.

System and method for rendering multi-dimensional data for identifying marker features are described herein. The multi-dimensional data may originate from any domain, such as information technology (IT), biology, agriculture, demography, and banking. The multi-dimensional data may include a plurality of data points and a plurality of features associated with each of the data point. Further, the marker features may refer to those features of the data points that distinguish a first subset of the multi-dimensional data from a second subset thereof. The marker features may also be understood as the features that may be responsible for clustering of the data points in a particular region. The clustering of the data points may indicate similarity between the data points of the multi-dimensional data.

Obtaining meaningful information from visualization is a challenge in visual data mining. Various visualization techniques have been used to visually provide results obtained from various computations based on the multi-dimensional data. Such visualization techniques tend to provide aggregate information and may prevent extraction of relevant information related to interrelations between various attributes or features of the multi-dimensional data. The term attributes may be understood as characteristics of the multi-dimensional data. In addition, some visualization techniques display multi-dimensional data that may be class labelled, i.e. categorized in classes and may not be efficient in representing non-class labelled multi-dimensional data. Typically, in case of the class labelled multi-dimensional data, a visualization technique, for example VizRank, may first rank all possible projections of the data points using different combinations of the features. VizRank may thereafter identify the best dimensional arrangement of the features based on the ranks assigned earlier. However, VizRank cannot be applied to non-class labelled multi-dimensional data.

The visualization techniques currently available for visualizing non-class labelled multi-dimensional data may include scatterplots, parallel coordinates, and circular layouts. However, the scatterplots and the parallel coordinates are found to be limited due to inability to visualize multi-dimensional data having a large number of associated features. The visualization technique involving the circular layouts, such as Radviz, may evenly place the features of the multi-dimensional data on a circle in no particular order. The data points of the multi-dimensional data may then be positioned inside the circle in such a way that the position of each data point is dependent on the relative values of the features. However, by placing the features uniformly on the circle circumference without any order, Radviz assumes the features to be independent. Furthermore, Radviz assumes all the features of the multi-dimensional data to be equally important which may not always be the case. In other words, Radviz ignores contributions of individual features of the multi-dimensional data and therefore does not provide an accurate depiction of the multi-dimensional data. Further, none of the above mentioned techniques available for the visualization of non-class labelled multidimensional data facilitate the identification of marker features specific to different subsets of the data points.

In various implementations, the present subject matter discloses a system and a method for identifying marker features of one or more subsets of multi-dimensional data. Each subset of the one or more subsets may include a plurality of data points associated with a plurality of features. Further, each of the plurality of data points may be defined by feature values corresponding to the associated features. For a given multi-dimensional (or multi-featured) data, the system may facilitate identification of a plurality of feature pairs based on a matrix of the plurality of data points and the plurality of features. In an implementation, if the matrix reflects an uneven distribution of the feature values of the plurality of features across the plurality of data points, the feature values may be normalized. The normalization may include converting the feature values of each of the plurality of features into corresponding standard score, such as z-score, values. In another implementation, the z-score values of each of the plurality of features may not be required if the matrix indicates an even distribution of the feature values.

Thereafter, the system may compute correlation co-efficient values between features in each of the plurality of feature pairs. In an implementation, the correlation co-efficient values may be computed by using Pearson Correlation. The system may also facilitate computation of correlation distances between features in each of the plurality of feature pairs. The correlation distances corresponding to each of the feature pairs may be calculated by subtracting the correlation co-efficient values for each of the plurality of feature pair from 1. For example, a lower correlation distance between the features may indicate a highly related feature pair. The correlation distances as computed may be used for arranging the plurality of features in a linear pattern, such that the features with low correlation distance are placed closer to each other while the features having high correlation distance are placed farthest. To do so, the plurality of features may be randomly flagged to distinguish each of the plurality of features.

Thereafter, a cut-off value may be defined based on the correlation distances between the features in each of the plurality of feature pairs. The cut-off value may be defined either empirically or dynamically by analyzing the correlation distances between each of the plurality of features. For a selected feature, other features that may have a correlation distance equal to or less than the initial cut-off value from the selected feature may be identified and grouped together. In an implementation, the selected feature may be considered as a representative of this group. Similarly, another selected feature may be grouped with all those features that may have the correlation distance equal to or less than the initial cut-off value from the another primary feature.

Accordingly, the system may facilitate creation of a plurality of groups of flagged features based on the selected features obtained from each of the plurality of features. The plurality of groups may include a set of features having a correlation distance equal to or less than the cut-off value from the primary feature of respective groups. It should be noted that if the second flagged feature is grouped in the first group represented by the first flagged feature, the second flagged feature may not be counted while forming another group. Similarly, all those features that have been included in the first group may not be considered while creating the remaining groups. Therefore, each of the plurality of groups includes a unique set of flagged features.

Once all the unique flagged features have been grouped, the initial cut-off value may be incremented by a factor 'i'. With the new cut-off value, the plurality of flagged features may be grouped again as described above. It will be evident to a person skilled in the art that the number of groups resulting after incrementing the cut-off value will be less than the number of groups before incrementing the cut-off value. Furthermore, the cut-off value may be incremented by the factor 'i' unless one big group containing all the flagged features is obtained. The order of formation of groups of flagged features obtained at each step is tracked for later use. Thereafter, each of the plurality of features may be aligned in the linear pattern by tracing back the order of formation of groups (of flagged features) as well as the correlation distances between each of the plurality of features.

Subsequently, a non-linear pattern, such as a semi-circle, of each of the plurality of features of the multi-dimensional data may be generated in a two-dimensional plane from the linear pattern. In other words, the linear pattern may be geometrically transformed into the non-linear pattern. The non-linear pattern may be based on the correlation distances such that the features in the highly related feature pair are placed closer to each other than the features not highly related to each other. For example, linear arrangement of each of the plurality of features may be transformed into a semi-circular arrangement that may be mapped with the non-linear pattern. The semi-circular arrangement is incorporated in order to ensure that the most uncorrelated features are placed at the diametrically opposite ends of the semi-circle. Once the plurality of features are mapped on to the non-linear pattern in accordance with the correlation distances between each of the plurality of features, the plurality of data points of the multi-dimensional data may be placed within a region bounded by the non-linear pattern.

In an implementation, each of the plurality of data points is placed based on the features that may be present in the data points. For example, each of the features may be considered to exert an attractive force on the data points. The magnitude of the force exerted by a feature on a data point may be based on the abundance of that feature in that data point. Therefore, the force exerted by each feature on each data point may be considered to be a force vector. Accordingly, the force exerted on each of the plurality of data points by each of the plurality of features may be evaluated. Based on the resultant force, each of the plurality of data points may be positioned within the region bounded by the non-linear pattern. It will be understood that the features that may be more prevalent in the data points may exert more force on the data points and therefore the data points may be placed near such features in the region bounded by non-linear pattern.

The present system may facilitate drawing inferences from the above described placement of features across the non-linear pattern and the positioning of each of the plurality of data points within the region. In an implementation, for a given multi-dimensional data set, the system may facilitate the differential clustering of the data points into sub-sets and interpreting causes of the differential clustering of the plurality of data points based on the variations in the features across the data points of a given subset. In an implementation, for the given subset, the system may calculate a threshold feature value for the associated features of the data points of the subset. This threshold feature value is calculated as the overall mean of all the features for the selected sub-set of data points. Further, a minimum value (lower bound) and a maximum value (upper bound) corresponding to each feature may be identified for the selected sub-set of data points and then plotted in a non-linear pattern in the two dimensional plane. The system may further represent the threshold feature value as a threshold non-linear pattern in the two-dimensional plane. In accordance with the threshold non-linear pattern each of the features of the data points in the given subset may be positioned in the two-dimensional plane based on its mean value for selected sub-set of data points The threshold non-linear pattern may facilitate in determining the marker features that may be responsible for the variations in the data points of the subset. The marker features may be identified for a given sub-set on the basis of the relative position of the features with respect to the threshold feature value in the two-dimensional plane and may be compared across different sub-sets of data points belonging to the same multi-dimensional data set.

In another implementation, the present subject matter facilitates in reducing dimensions of the multi-dimensional data. The dimension reduction may be performed by using an evaluation plot approach. In this approach, an evaluation plot may be generated for the plurality of features of the multi-dimensional data. Based on the groups of the features that are obtained at various cut-off values, as explained earlier, similarity between each of the plurality of features may be identified. Alternatively, the dimension reduction may be performed by using a correlation based filtering approach. In this approach, only one feature from a highly correlated feature pair may be selected to be plotted on the non-linear pattern.

The present subject matter renders the multi-dimensional data in the two-dimensional plane for efficiently visualizing large volumes of non-class labelled data containing a multitude of features. The grouping of the plurality of features as explained above reduces the time taken for arranging the plurality of features. Further, the plurality of features may be arranged on a circumference of the non-linear pattern based on the correlation distances between each of the plurality of features. This may ensure that the contribution of each of the plurality of features is given appropriate weightage for enabling meaningful visualization of the non-class labelled data.

The combination of the above mentioned functionalities as provided in the present subject matter provides an informative visualization of relationships between the data points and the features in the non-class labelled data. The representation of the multi-dimensional data in the two-dimensional plane may facilitate in identifying the grouping pattern within the data points of the multi-dimensional data. The system may also provide information about the marker features specific for each subset of the data points.

These and other advantages of the present subject matter would be described in greater detail in conjunction with the following figures. While aspects of described systems and methods for rendering multi-dimensional data to identify marker features can be implemented in any number of different computing systems, environments, and/or configurations, the embodiments are described in the context of the following exemplary system(s).

FIG. 1 illustrates a network environment 100 implementing a feature identification system 102, in accordance with an embodiment of the present subject matter. In said embodiment, the network environment 100 includes the feature identification system 102 configured to identify marker features in one or more subsets of a multi-dimensional data. The multi-dimensional data may include a plurality of data points associated with a plurality of features. Further, each of the plurality of data points may be defined by feature values corresponding to the associated features. Furthermore, the marker features may be understood as those features that may be responsible for variation in features associated with data points of the one or more subsets. Additionally, the marker features may be responsible for formation of clusters between the plurality of data points of the multi-dimensional data.

In one implementation, the network environment 100 may be a company network, including thousands of office personal computers, laptops, various servers, such as blade servers, and other computing devices. Examples of a company may include an information technology (IT) company, a product manufacturing company, a human resource (HR) company, a telecommunication company, or other large conglomerates. It will also be appreciated by a person skilled in the art that the company may be any company involved in any line of business. In another implementation, the network environment 100 may be a smaller private network. In yet another implementation, the network environment 100 may be a public network, such as public cloud.

The feature identification system 102 may be implemented in a variety of computing systems, such as a laptop computer, a desktop computer, a notebook, a workstation, a mainframe computer, a server, a network server, and the like. In one implementation, the feature identification system 102 may be included within an existing information technology infrastructure or a database management structure. Further, it will be understood that the feature identification system 102 may be connected to a plurality of user devices 104-1, 104-2, 104-3, . . . , 104-N, collectively referred to as the user devices 104 or as an individual user device 104. The user device 104 may include, but is not limited to, a desktop computer, a portable computer, a mobile phone, a handheld device, and a workstation. The user devices 104 may be used by users, such as database analysts, programmers, developers, data architects, software architects, module leaders, projects leaders, database administrator (DBA), stakeholders, and the like.

As shown in the figure, the user devices 104 are communicatively coupled to the feature identification system 102 over a network 106 through one or more communication links for facilitating one or more end users to access and operate the feature identification system 102. In one implementation, the network 106 may be a wireless network, a wired network, or a combination thereof. The network 106 may also be an individual network or a collection of many such individual networks, interconnected with each other and functioning as a single large network, e.g., the Internet or an intranet. The network 106 may be implemented as one of the different types of networks, such as intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), etc., to communicate with each other. Further, the network 106 may include a variety of network devices, including routers, bridges, servers, computing devices, storage devices, and the like.

In an implementation, the feature identification system 102 may be coupled to a database 108. Although not shown in the figure, it will be understood that the database 108 may also be connected to the network 106 or any other network in the network environment 100. In an implementation, the database 108 may include various input files containing the multi-dimensional data that may be required by the feature identification system 102. In an implementation, the database 108 may be provided as a relational database and may store data in various formats, such as relational tables, object oriented relational tables, indexed tables. However, it will be understood that the database 108 may be provided as other types of databases, such as operational databases, analytical databases, hierarchical databases, and distributed or network databases.

The feature identification system 102 further includes interface(s) 112, for example, to render the multi-dimensional data in a two-dimensional plane. Further, the interface(s) 112 may include a variety of software and hardware interfaces, for example, interfaces for peripheral device(s), such as a keyboard, a mouse, an external memory, and a printer. Additionally, the interface(s) 112 may enable the feature identification system 102 to communicate with other devices, such as web servers and external repositories. The interface(s) 112 may also facilitate multiple communications within a wide variety of networks and protocol types, including wired networks, for example, LAN, cable, etc., and wireless networks, such as WLAN, cellular, or satellite. For the purpose, the interface(s) 112 may include one or more ports.

In an implementation, the feature identification system 102 includes a processor(s) 110 coupled to a memory 114. The processor(s) 110 may be implemented as one or more microprocessors, microcomputers, microcontrollers, digital signal processors, central processing units, state machines, logic circuitries, and/or any devices that manipulate signals based on operational instructions. Among other capabilities, the processor(s) 110 may be configured to fetch and execute computer-readable instructions stored in the memory 114.

The memory 114 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. Further, the memory 114 includes module(s) 116 and data 118.

The module(s) 116 include, for example, a computation module 120, a rendering module 122, and other module(s) 124. The other module(s) 124 may include programs or coded instructions that supplement applications or functions performed by the feature identification system 102.

The data 118 may include feature data 126, correlation data 128, group data 130, and other data 132. The other data 132, amongst other things, may serve as a repository for storing data that is processed, received, or generated as a result of the execution of one or more modules in the module(s) 116. Although the data 118 is shown internal to the feature identification system 102, it may be understood that the data 118 can reside in an external repository (not shown in the figure), which may be coupled to the feature identification system 102. The feature identification system 102 may communicate with the external repository through the interface(s) 112 to obtain information from the data 118.

As mentioned herein, the present subject matter discloses a system and a method for identifying marker features of one or more subsets of multi-dimensional data. Each subset of the multi-dimensional data may include a plurality of data points that may be associated with a plurality of features. Further, each of the plurality of data points may be defined by feature values that may correspond to the associated features. In addition, the marker features may refer to those distinguishing feature that may be responsible for variation in behaviour of a subset of the multi-dimensional data from amongst the one or more subsets.

According to an implementation, the computation module 120 may be configured to identify a plurality of feature pairs based on a matrix between the plurality of data points and the plurality of features. The matrix may be generated by the computation module 120 based on an input file that may be stored in the database 108. The input file may include multi-dimensional data. The matrix may be understood as a summary of the multi-dimensional data. In an implementation, a user may select the input file through the user device 104 from the database 108. Further, a parser may be employed for generating the matrix from the input file. The parser may be understood as a program, such as part of a compiler that receives an input in a defined format and may break the input into parts that can then be managed by other programming components. The computation module 120 may also be configured to store the features as feature data 126. The feature data 126 may include relationship between the features and the data points along with the feature values associated with the features.

Further, the matrix may facilitate the computation module 120 to assess distribution of the plurality of features across the plurality of data points. In another implementation, the computation module 120 may generate the matrix by calculating mean values of each feature associated with the multi-dimensional data. In an example, if the mean of the feature values associated with the one or more features indicate little variation across the one or more data points, the feature values may not be required to be normalized. On the other hand, if the mean values of one or more features indicate huge variations amongst the data points, the computation module 120 may normalize the feature values. To do so, the feature values may be transformed into corresponding standard score (z-score) values. The z-score values may be calculated by using the formula:

$$z = \frac{x - M}{S.D}$$

where, x is a feature value to be normalized, M is a mean value of the one or more feature values in the multi-dimensional data, and S.D is the standard deviation of the multi-dimensional data.

In another implementation, the computation module 120 may further be configured to obtain correlation co-efficient between each of the plurality of feature pairs. In the present implementation, Pearson Correlation may be employed for obtaining the correlation co-efficient between the feature pairs. The Pearson Correlation may be obtained based on the feature values across the one or more data points. The correlation co-efficient may be computed by using the formula:

$$r_{xy} = \frac{\sum_{i=1}^{n}(x_i - M_x)(y_i - M_y)}{\sqrt{\sum_{i=1}^{n}(x_i - M_x)^2 \sum_{i=1}^{n}(y_i - M_y)^2}}$$

where, $r_{xy}$ may indicate a degree of linear relationship between the features in each of the feature pairs. $x_i$ and $y_i$ are relative feature values for features x and y for the ith data point (where i=1, 2, ... n) and $M_x$ and $M_y$ are the mean values of the relative feature values of x and y features across the data points. The value of r may vary from −1 to +1 where a correlation co-efficient of −1 indicates a perfect negative relationship between the features of a feature pair and a correlation co-efficient of +1 indicates a perfect positive relationship between the features of a feature pair. Moreover, a correlation co-efficient of 0 indicates that the features in the feature pair are not related to each other.

It will be evident to a person skilled in the art that though the computation module 120 of the present subject matter employs Pearson Correlation for computing the correlation co-efficient between the features, other distance matrices, such as Euclidean matrix, Bray-Curtis matrix, and Hellinger distance matrix may be employed by the computation module 120.

Thereafter, the computation module 120 may compute a correlation distance between the features of each of the feature pairs by subtracting the correlation co-efficient values from 1. This may provide pair wise correlation distance between all the features of the multi-dimensional data. The correlation distance may indicate a relationship between the features. For example, a lower correlation distance between features of a feature pair may indicate that the feature pair is highly related. The computation module 120 may further be configured to store the correlation distance between the features of all the feature pairs as correlation data 128. The correlation data 128 may indicate the correlation distance between the features of each of the feature pairs. In an implementation, the correlation data 128 may be saved in the form of a distance matrix. The correlation distances may be saved in pairs for the feature pairs corresponding to the data points.

In another implementation, the computation module 120 may be configured to arrange the features of the multi-dimensional data in a linear pattern based on the correlation distances between the features of the feature pairs. In the present implementation, the features may be randomly flagged to distinguish between each of the features. Thereafter, a first flagged feature may be selected and the correlation distances between the first flagged feature (F1) from all other flagged features may be extracted. It will be understood that the computation module 120 may extract the correlation distances from the correlation data 128. Moreover, the computation module 120 may determine a cut-off (c) value based on which the features may be arranged in a linear pattern. The 'c' value may be calculated empirically or may be identified on the basis of the distance matrix stored in the correlation data 128. For example, the 'c' value may be $\frac{1}{5}^{th}$ of the mean value of the distances that may be stored in the distance matrix.

Upon identification of the 'c' value, the features within a distance 'c' from F1 may be identified and grouped together. The group may be named as F1 to indicate F1 as a representative feature of the group. In an implementation, the flagged features that are a part of the F1 group will not be considered while formation of other similar groups. Further, representation of the group by a feature may prevent re-calculation of the correlation distances between the features. Accordingly, this may reduce the computation time that may otherwise be required at each step. The computation module 120 may thereafter select a second flagged feature (F2) if not a part of the F1 group. As described above, all features that may be lying within a distance of 'c' from F2 may be identified and grouped together to obtain a F2 group. In a similar manner, all unique features (not a part of earlier groups) are selected one by one and groups are formed on the basis of the 'c' value. Once, all the features have been grouped together, the computation module 120 may increment the 'c' value by a small fraction. For example, 'c' value may be incremented by fraction of 0.001. Thereafter, the above described process of formation of groups based on the features within a radius of the incremented 'c' value from the uniquely flagged features is performed and the groups are obtained. The process of incrementing the 'c' value by the small fraction and formation of groups is repeated until one big group containing all the features is obtained.

Further, the computation module 120 may be configured to store the various 'c' values and the corresponding number of groups as group data 130. In an implementation, the group data 130 may store positional information corresponding to all features of all the groups, such as distance between each feature of a group. In an implementation, linear coordinates of the features may be identified using a hierarchical clustering technique that may involve analysis of clusters for obtaining a hierarchy between the clusters. However as mentioned above, the hierarchical clustering technique may require more computation time as compared to the above described steps.

Thereafter, the computation module 120 may arrange the features in the linear pattern by progressively extracting the positional information of each group. The positional information of each group may include relative distance between each feature of each group. Accordingly, the computation module 120 may facilitate in obtaining an optimal arrangement of the features in the linear pattern, such that the highly correlated features may be placed closer to each other than the features that may be least correlated. In an implementation, the linear pattern may be a line and the positions of each of the features on the line may be represented as LINE_COORDINATES (X1, Y1). In the present subject matter, starting coordinates of the line may be (0, 0) and the features may be positioned as per the X1 value from a previous feature. The X1 value may be the distance between the features that may be obtained from the distance matrix of the correlation data 128. Further, the Y1 values may be considered as 0 for all the features.

In accordance with an implementation, the computation module 120 may further be configured to generate a non-linear pattern, such as a semi-circle, based on the linear arrangement of the features. The computation module 120 may represent the semi-circle in a two-dimensional plane. The computation module 120 of the present subject matter may facilitate in geometrically transforming the line coordinates into semi-circular coordinates. The computation module 120 may compute maximum and minimum values of the LINE_COORDINATES of each of the features based on the corresponding X values. The maximum and the minimum values for the features arranged on the line may be represented as (MAX1, MIN1), where MAX1 indicates maximum value of X coordinates and MIN 1 indicates the minimum value of X coordinates corresponding to the LINE_COORDINATES. Further, based on the (MAX1, MIN1) values, a radius (R) of the semi-circle may be computed as, $$R = \frac{(MAX1 - MIN1)}{2}$$

Accordingly, the computation module 120 may determine the coordinates of center of the semi-circle as (M1, M2), where M1=R and M2=0.

Thereafter, for each feature (F) of the plurality of features, the computation module 120 may transform the LINE_COORDINATES (X1, Y1) into corresponding CIRCLE_COORDINATES (X2, Y2). In an implementation, for transforming the line coordinates into the corresponding semi-circular coordinates, distance (D) of each feature (F) may be determined from the centre of the semi-circle (M1, M2). Further, the computation module 120 may calculate an angle (θ) that may be formed by the CIRCLE_COORDINATES of each of the feature with the centre of the semi-circle. For example, θ may be calculated by using the formula, $$\theta = \frac{(\pi * D)}{(MAX1 - MIN1)}, \text{ where, } \pi = 3.14$$

Subsequently, a new set of values (U, V) may be obtained for each of the features, where, $$U = R \sin \theta$$

$$V = R(1 - \cos \theta)$$

Based on the new set of values (U, V) for each of the features, as calculated above by the computation module 120, the transformed coordinates, i.e., the CIRCLE_COORDINATES (X2, Y2) may be obtained, as described below, for each feature (F) in the semi-circle. Accordingly, the CIRCLE_COORDINATES (X2, Y2) may be obtained as, if(X1>=M1,then X2=M1+U and Y2=M1−V else,X2=M1−U and Y2=M1−V Accordingly, the transformed set of coordinates may be obtained for each of the features of the multi-dimensional data. As will be understood, the transformed set of coordinates is obtained on the basis of the correlation distances of the features. For example, the features in the highly related feature pair are placed close to each other on the semi-circle than the features that may not be highly related to each other. Referring to FIG. 1a, a non-linear pattern 100-1 of the features 134 of the multi-dimensional data in a two-dimensional plane is illustrated, in accordance with an embodiment of the present subject matter. As depicted in FIG. 1a, the features 134 are arranged across the circumference of the semi-circle based on the correlation distance amongst each of the features.

Additionally, the data points may be positioned inside a region bounded by the semi-circle. In an implementation, the computation module 120 of the present subject matter may use Hooke's Law to restrict the data points within the region defined by the semi-circle. To do so, the computation module 120 may evaluate the attractive force exerted on each of the data points by each of the features as explained below. Firstly, maximum and minimum values (MAX2, MIN2) of the CIRCLE_COORDINATES of the features may be obtained as described with respect to the LINE_COORDINATES, where MAX2 may indicate a maximum distance between adjacent features and MIN2 may indicate a minimum distance between adjacent features as represented on the semi-circle. Upon identification of the (MAX2, MIN2), start coordinates (X3 Y3) and end coordinates (X4, Y4) of the semi-circle may be determined as (MIN2, 0) and (MAX2, 0) respectively.

Accordingly, the coordinates of the centre of the semi-circle may be represented as (C1, C2) which may correspond to, $$C1 = \frac{(X3 + X4)}{2}$$

$$C2 = \frac{(Y3 + Y4)}{2}$$

Based on the coordinates (C1, C2) of the centre of the semi-circle, the radius (R) of the semi-circle may correspond to,

R={(X4−C1)*2+(Y4−C2)*2}

Further, to identify the position of each data point within the semi-circle, imaginary coordinates for the data points may be defined as $(T_x, T_y)$. Further, four variables may be defined as $U_{num}$, $U_{den}$, $V_{num}$, and $V_{den}$ that may be assigned an initial value of zero. The computation module 120 may compute the force exerted on each data point (P) due to each of the features (F). The force may be computed by identifying a maximum and a minimum value (MAX_P, MIN_P) for each P for all the features. Further, for each feature (F) that may belong to the CIRCLE_COORDINATES (X2, Y2), distance (D1) of each data point P may be determined from the center of the circle, i.e., (C1, C2). Additionally, distance (D2) may be determined from the end coordinates (X4, Y4) of the semi-circle. Based on the above determined distances, D1 and D2, and angle alpha (α) that may be made by each data point P with the center (C1, C2) may be obtained as:

$$\cos\alpha = \frac{(D1^2 + D2^2 - D3^2)}{(2*D1*D2)}$$

Moreover, the value of each of the data point P may be normalized so that a value between 0 and 1 may be obtained. Considering an absolute value of feature F in each data point P as SF, the normalized value for the feature F may be calculated as:

$$NSF = \frac{(SF - MIN\_P)}{(MAX\_P - MIN\_P)}$$

Once the normalized value for each of the feature is obtained, $U_{num}$, $U_{den}$, $V_{num}$, and $V_{den}$ may be calculated by the computation module 120 as:

$$U_{num} = U_{num} + (NSF * \cos\alpha)$$

$$U_{den} = U_{den} + NSF$$

$$V_{den} = V_{num} + (NSF * \sin\alpha)$$

$$V_{den} = V_{den} + NSF$$

Accordingly, the coordinates of each data point P inside the semi-circle may be obtained as:

$$T_x = \frac{U_{num}}{U_{den}}$$

$$T_y = \frac{V_{num}}{V_{den}}$$

Figure 1B:
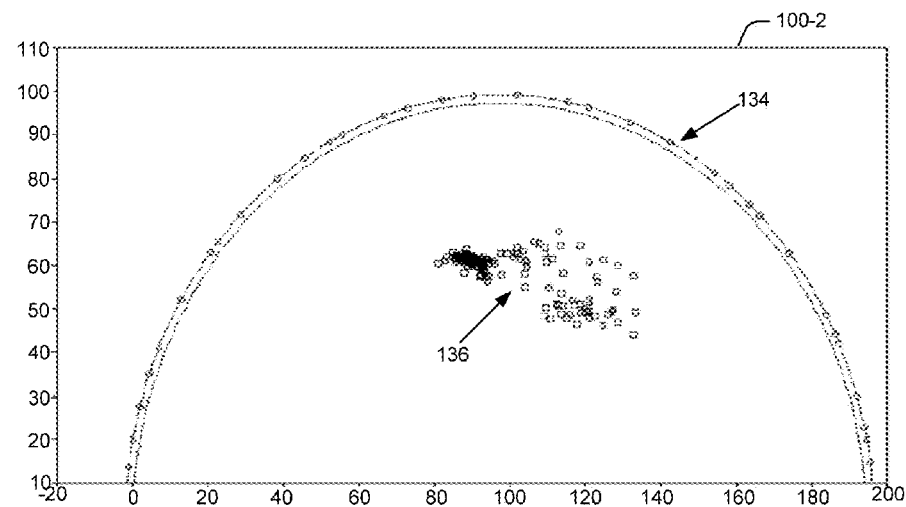
FIG. 1b illustrates positioning of the data points within the non-linear pattern in the two-dimensional plane, in accordance with an embodiment of the present subject matter.

Referring to FIG. 1b, positioning of the data points 136 within the non-linear pattern 100-2 in the two-dimensional plane is illustrated, in accordance with an embodiment of the present subject matter. The data points 136 are projected inside the semi-circle on the basis of the abundance of features 134 in the data points 136.

In another implementation, the semi-circle as depicted in FIG. 1b illustrates the features 134 and the data points 136 belonging to the multi-dimensional data. As mentioned above, the multi-dimensional data may include one or more subsets of data. The data points 136 may therefore collectively refer to the data points of the one or more subsets. The present subject matter facilitates identification of variation amongst the features belonging to data points of the one or more subsets.

Figure 1C:
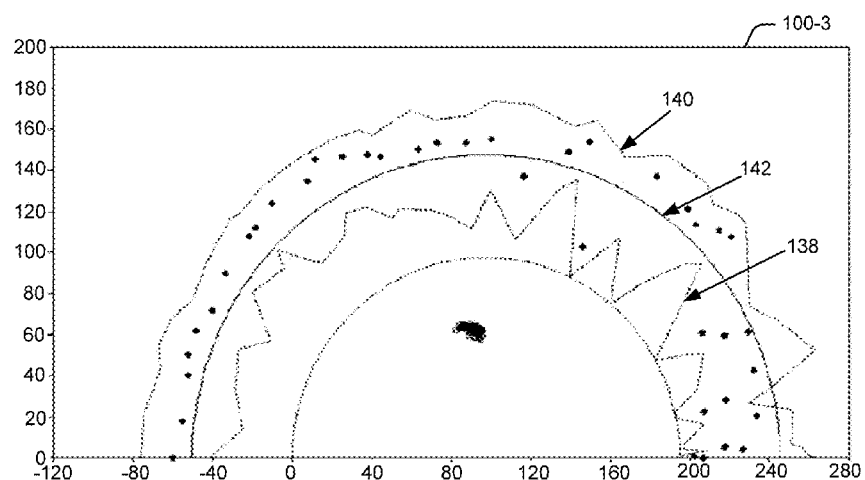
FIG. 1c illustrates a feature variation plot, in accordance with an embodiment of the present subject matter.

Referring to FIG. 1c, a feature variation plot 100-3 is illustrated, in accordance with an embodiment of the present subject matter. Referring again to FIG. 1, the rendering module 122 may be configured to identify minimum feature values, such as a lower limit 138, across the data points of a subset of the one or more subsets. Further, the rendering module 122 may also identify maximum feature values, such as an upper limit 140, across the data points of the subset. In addition, the rendering module 122 may calculate a threshold feature value for the associated features of the data points of the subset. The threshold feature value may be understood as a mean value of mean of the feature values across the data points.

The rendering module 122 may represent the threshold feature value as a threshold non-linear pattern 142 in the two-dimensional plane. For example, based on the threshold feature value, a semi-circle may be generated in the two-dimensional plane. Further, the rendering module 122 may be configured to position the features of the data points in the subset with respect to the threshold feature value in the two-dimensional plane. This may facilitate in visualizing the variations in the features of the subset. For example, based on their individual mean values for the subset of data points, the features may be distributed near the threshold non-linear pattern 142, near the lower limit 138, and near the upper limit 140 of the subset in the two-dimensional plane. Such a distribution may indicate that the features lying far off from the threshold non-linear pattern 142 are responsible for the variations in the subset. In other words, the features may either be near the lower limit 138 or near the upper limit 140 to be far off from the threshold non-linear pattern. Accordingly, the rendering module 122 may identify such features as the marker features for the subset.

Figure 1D:
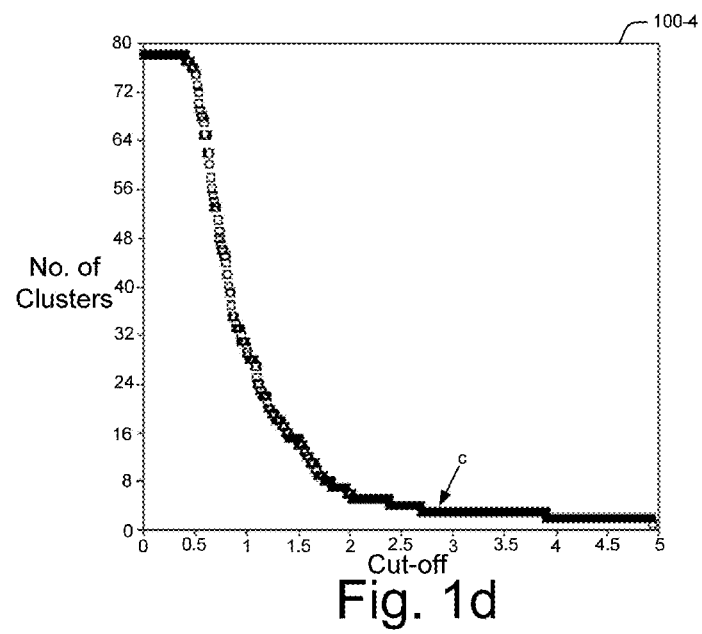
FIG. 1d illustrates a dimension reduction plot of the features, in accordance with an embodiment of the present subject matter.

Referring to FIG. 1d, a dimension reduction plot 100-4 of the features is illustrated, in accordance with an embodiment of the present subject matter. In an implementation, the rendering module 122 may further be configured to perform the dimension reduction function on the multi-dimensional data by using one of an evaluation plot technique and a correlation filtering technique. The evaluation plot technique may include generation of a plot using the number of groups as stored in the group data 130 and at various 'c' values. The evaluation plot may facilitate in determining extent of similarity between various groups that may be formed at different 'c' values. For example, the evaluation plot 100-4 may indicate that after a certain 'c' value, the number of groups formed by the features remains similar. This observation may be exploited to reduce the number of features and subsequently generate the non-linear pattern with a reduced set of features.

In an alternate implementation, the correlation based filtering technique may be employed for dimensionality reduction. In this technique, one member of a highly correlating pair, for example having correlation more than 0.9, may be selected and chosen as a feature on the non-linear pattern.

Accordingly, the present subject matter represents the multi-dimensional data in the two-dimensional plane for efficient visualization of large volumes of non-class labelled data containing a multitude of features. The grouping of the plurality of features as explained above reduces the time taken for arranging the plurality of features. Further, the plurality of features may be arranged on the circumference of the non-linear pattern based on the correlation distances between each of the plurality of features. This may ensure that the contribution of each of the plurality of features is given appropriate weightage for enabling meaningful visualization of the non-class labelled data. Additionally, the representation of the multi-dimensional data in the two-dimensional plane may facilitate in identifying the grouping pattern within the data points of the multi-dimensional data.

Figure 2A:
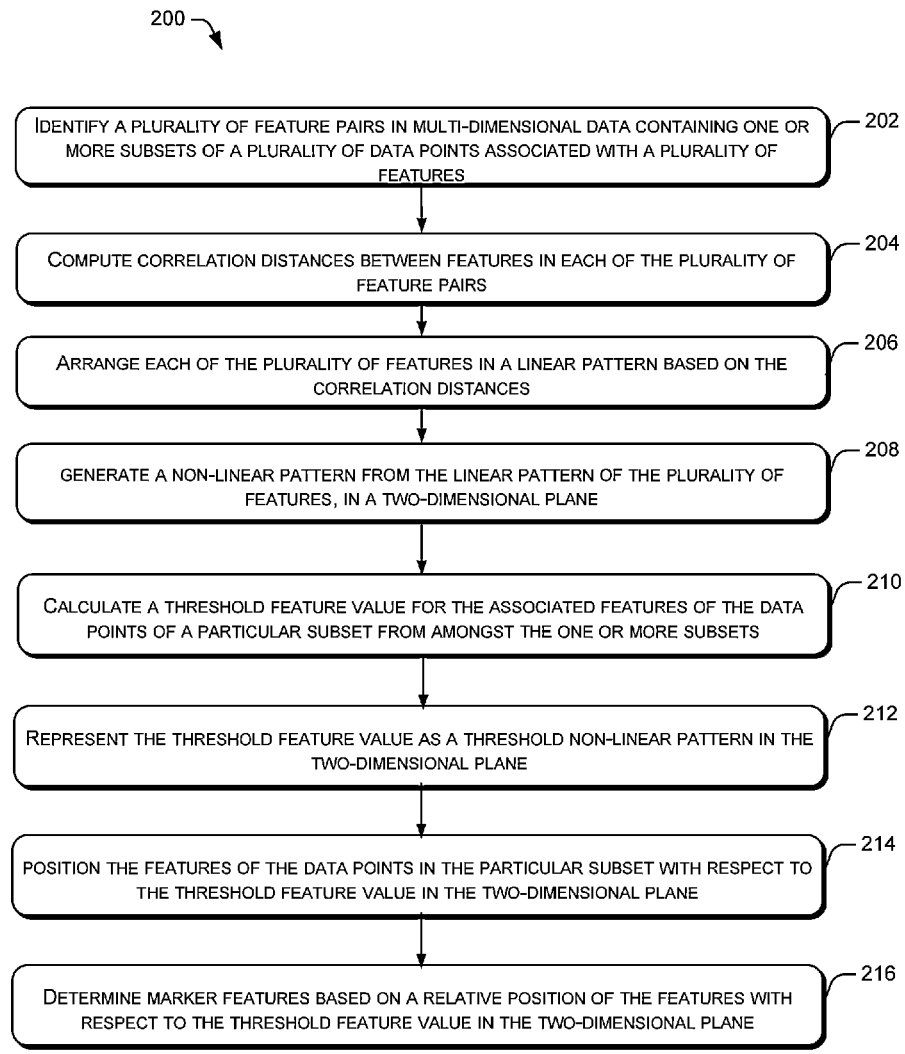
FIG. 2a shows a flowchart illustrating a method for identifying marker features of one or more subsets of a multi-dimensional data, in accordance with an embodiment of the present subject matter.

FIG. 2a illustrates a method 200 for identifying marker features of one or more subsets of a multi-dimensional data, in accordance with an embodiment of the present subject matter. Each subset may include a plurality of data points associated with a plurality of features. Further, each of the plurality of data points may be defined by feature values corresponding to the associated features. The method 200 may be described in the general context of computer executable instructions. Generally, computer executable instructions can include routines, programs, objects, components, data structures, procedures, modules, functions that perform particular functions or implement particular abstract data types. The method 200 may also be practiced in a distributed computing environment where functions are performed by remote processing devices that are linked through a communication network. In a distributed computing environment, computer executable instructions may be located in both local and remote computer storage media, including memory storage devices.

The order in which the method 200 is described is not intended to be construed as a limitation, and any number of the described method blocks can be combined in any order to implement the method 200 or alternative methods. Additionally, individual blocks may be deleted from the method 200 without departing from the spirit and scope of the subject matter described herein. Furthermore, the method 200 can be implemented in any suitable hardware, software, firmware, or combination thereof.

At block 202, a plurality of feature pairs may be identified, for example, by the computation module 120 of the feature identification system 102. The plurality of feature pairs may be identified based on a matrix between the plurality of data points and the plurality of features. The matrix may be understood as a summary of the multi-dimensional data. The computation module 120 may be configured to store the features of the multi-dimensional data as feature data 126.

At block 204, correlation distances between features in each of the plurality of feature pairs may be computed, for example, by the computation module 120. The correlation distances may be computed on the basis of correlation co-efficient between each of the plurality of feature pairs. The computation module 120 may employ the Pearson's correlation to compute the correlation co-efficient for each of the feature pairs. Thereafter, the correlation distance may be calculated from the correlation co-efficient by subtracting the correlation co-efficient from 1. Further, the computation module 120 may be configured to store the correlation distance between each of the feature pairs in the form of a distance matrix as correlation data 128.

At block 206, each of the plurality of features may be arranged in a linear pattern. The computation module 120 may arrange each of the plurality of features in the linear pattern based on the correlation distances between each of the features. The arrangement of the features in the linear pattern will be explained in details in conjunction with FIG. 2b.

At block 208, a non-linear pattern may be generated from the linear pattern of the plurality of features, in a two-dimensional plane. The computation module 120 may transform linear coordinates of the plurality of features into corresponding circular coordinates. In an implementation, the non-linear pattern may be a semi-circular pattern, such that each of plurality of features may be arranged across the circumference of the semi-circle based on the correlation distances between the features. For example, features having low correlation distance may be placed closer to each other as compared to features having high correlation distance. The non-linear pattern may facilitate positioning the least correlated features at two ends of the semi-circle.

Further, the computation module 120 may be configured to position the plurality of data points of the multi-dimensional data inside a region bounded by the semi-circle. The computation module 120 may evaluate an attractive force that may be imagined to be exerted on each of the data points from each of the plurality of features. Based on the evaluation, the data points may be positioned inside the semi-circle.

At block 210, a threshold feature value for associated features of data points of a particular subset from amongst the one or more subsets may be calculated. The rendering module 122 of the feature identification system 102 may be configured to compute a lower limit, an upper limit, and the threshold feature value for the one or more subsets. In an implementation, the threshold feature value may be understood as a mean of the mean values of all features across the data points of the particular subset.

At block 212, the threshold feature value may be represented as a threshold non-linear pattern in the two-dimensional plane. The rendering module 122 may represent the threshold non-linear pattern as another semi-circle in the two-dimensional plane.

Further, at block 214, the features of the data points in the particular subset may be positioned with respect to the threshold feature value in the two-dimensional plane. In one implementation, this placement may be determined based on the mean values of the individual features for the subset of data points.

At block 216, the marker features may be determined based on a relative position of the features with respect to the threshold feature value in the two-dimensional plane. For example, the features that may be positioned far off from the threshold non-linear pattern may be identified as the marker features by the rendering module 122. The marker features may be understood as the features that may be responsible for variations in the one or more subsets of the multi-dimensional data. Additionally, the marker features may also be understood as the features that may be responsible for the differential clustering of the data points of the multi-dimensional data.

Figure 2B:
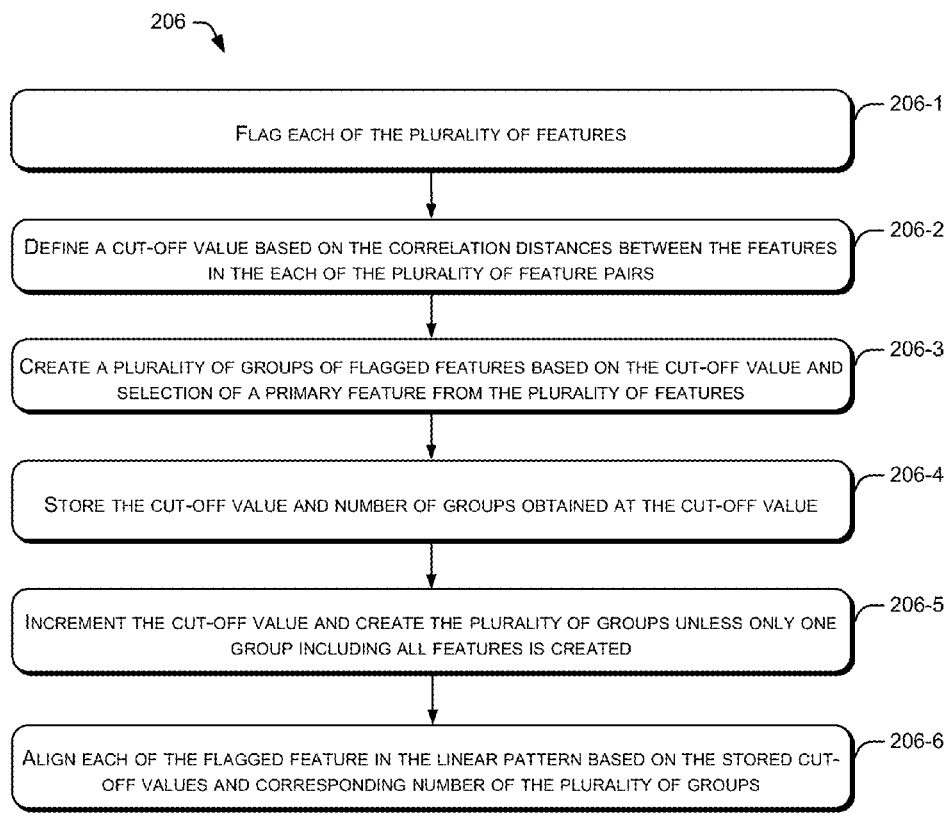
FIG. 2b shows a flowchart illustrating a method for aligning the plurality of features in the linear pattern, in accordance with an embodiment of the present subject matter.

Referring to FIG. 2b, a flowchart for a method 206 for aligning the plurality of features in the linear pattern is illustrated, in accordance with an embodiment of the present subject matter. At block 206-1, each of the plurality of features may be flagged, for example, by the computation module 120. The flagging of the plurality of features may be understood as providing a unique identity to each of the plurality of features.

At block 206-2, a cut-off value may be defined based on the correlation distances between the features in each of the plurality of feature pairs. The computation module 120 may be configured to compute the correlation distances between the features, as explained above. In an implementation, the cut-off value may be calculated empirically by determining $1/5^{th}$ of the mean value of the correlation distances.

At block 206-3, based on the cut-off value, a plurality of groups of the flagged features may be created. For example, the computation module 120 may select a primary feature and identify the flagged features that may have correlation distance equal to or less than the cut-off value. Based on the identification, the computation module 120 may create the plurality of groups. In an implementation, each of the plurality of groups may include unique set of flagged features. This may facilitate in reducing the computation time that may be otherwise taken.

At block 206-4, the cut-off value and corresponding number of groups may be stored. For example, the computation module 120 may be configured to store the cut-off value and the number of groups obtained at the cut-off value as group data 130.

At block 206-5, the cut-off value may be incremented by a small factor 'i'. Further, for the incremented cut-off value, the plurality of groups of the flagged features, as described in block 206-3, may be created. Accordingly, the cut-off value may be incremented until one large group containing all the features is obtained.

At block 206-6, each of the plurality of flagged features may be aligned in the linear pattern. The computation module 120 may refer to the stored cut-off values and the corresponding number of groups of the flagged features that may be created at each cut-off value. Based on this information, each of the plurality of flagged features may be aligned on the linear pattern by the computation module 120.

Although embodiments for identification of the marker features in the multi-dimensional data have been described in language specific to structural features and/or methods, it is to be understood that the present subject matter is not necessarily limited to the specific features or methods described. Rather, the specific features and methods are disclosed as exemplary implementations for the feature identification system.

EXAMPLE CASE STUDIES

The applicability of the various functionalities of the feature identification system 102 pertains to the efficient resolution of non-class labelled multi-dimensional data. In an implementation, the applicability of various functionalities of the feature identification system 102 may be understood by using freely available biological data sets. Further, the biological data sets include class labelled data to validate capabilities of the feature identification system 102 for resolving multi-dimensional data into groups. In addition, the feature identification system 102 is examined to decipher group specific patterns that may be used to draw meaningful inferences about the data points.

The data set used as an example may include a first sample data set. The first sample data set may include gene expression data of 79 different micro-array experiments on budding yeast (*Saccharomyces cerevisiae*) under different conditions. These conditions may include diauxic shift, sporulation, and heat shock. From the gene expression data, 186 genes belonging to three functional subsets were considered for further analysis. The three subsets, namely, respiration (abbreviated as 'Resp'), cytoplasmic ribosomes (abbreviated as 'Ribo'), and proteasome (abbreviated as Proteas'), may be clustered on the basis of expression levels of the constituent genes corresponding to each of these subsets.

Figure 3A:
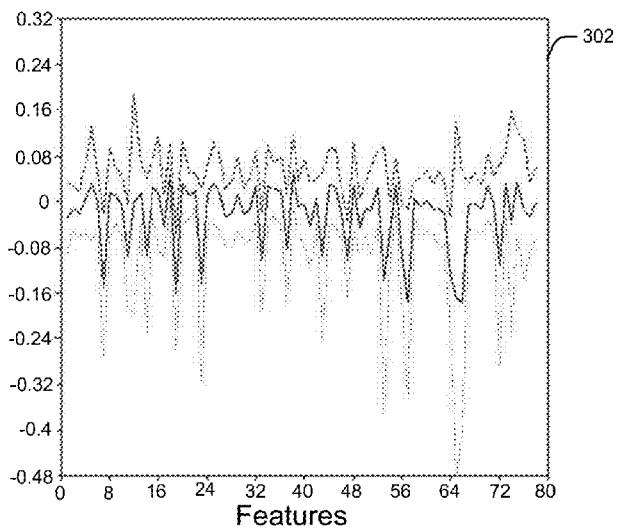
FIG. 3a illustrates variation of feature values across all data points belonging to a first sample data set, in accordance with an embodiment of the present subject matter.

FIG. 3a illustrates a plot 302 generated for the first sample data set, in accordance with an embodiment of the present subject matter. The plot 302 may be generated by the computation module 120 based on an input file. As described above, the first sample data set may be stored in the input file. For each feature, the computation module 120 calculates the mean feature value and its standard deviation across all data points. The plot 302 may provide a summary based on the input file. The plot 302 may indicate variation of the features across the data points of the first sample data set. Further, the plot 302 may facilitate in deciding whether to normalize the feature values of the first sample data set or not. In accordance with the first sample data set, normalization may not be required as the variation of the feature values is generally uniform. Therefore, a non-linear pattern may be generated in a two-dimensional plane for the plurality of features without normalization. In an implementation, a graphical user interface (GUI) of the feature identification system 102 may include a "Plot in Igloo" button that may be used for creating the non-linear pattern.

Figure 3B:
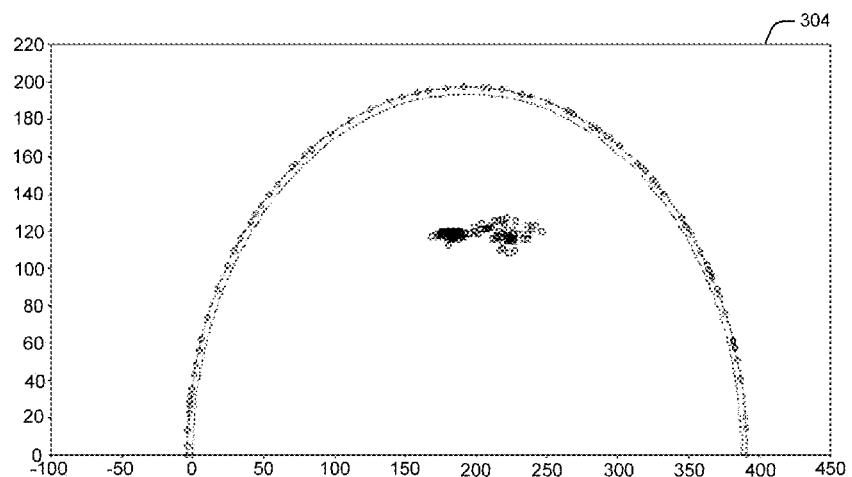
FIG. 3b illustrates a non-linear pattern generated for the first sample data set, in accordance with an embodiment of the present subject matter.

Referring to FIG. 3b the non-linear pattern 304, such as a semi-circle, may be generated for the first sample data set, in accordance with an embodiment of the present subject matter. As may be indicated by the non-linear pattern 304-1 the number of features is very high. Further, the data points may not seem to be sufficiently resolved in the semi-circle. Consequently, the number of features may need to be reduced to facilitate a better visualization of the data points.

Figure 3C:
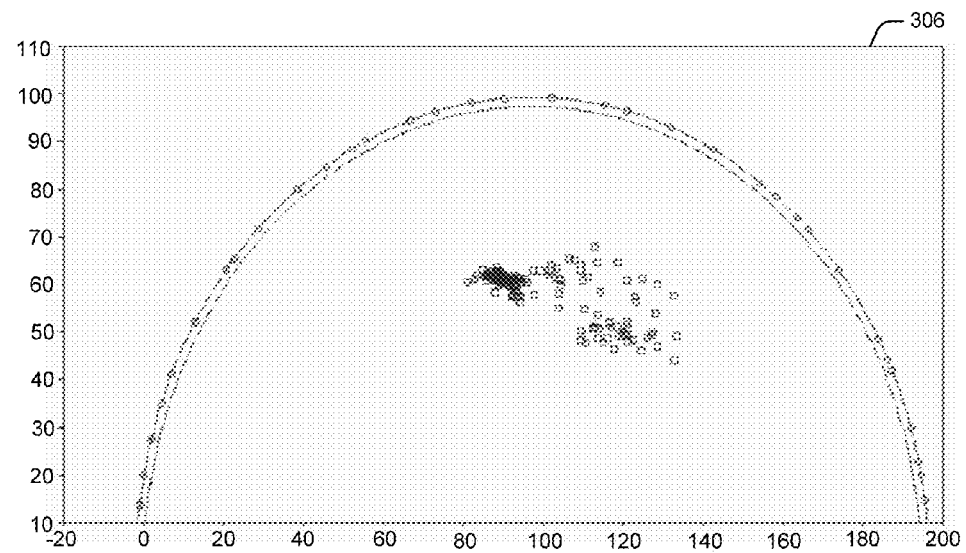
FIG. 3c illustrates the non-linear pattern generated with lesser number of features for the first sample data set, in accordance with an embodiment of the present subject matter.

Referring to FIG. 3c, a non-linear pattern 306 generated with lesser number of features for the first sample data set is illustrated, in accordance with an embodiment of the present subject matter. The rendering module 122 of the feature identification system 102 may be configured to reduce the number of features on the semi-circle and may generate a new semi-circle with a reduced set of features. Further, the feature identification system 102 may provide labels for the features on the semi-circle. Additionally, the rendering module 122 may provide three tabs, namely features, data points, and subsets which may be obtained from the input file. In an example, if the data points are selected and name of a particular subset, such as 'Ribo' may be specified, the feature identification system 102 may highlight all the data points names starting with 'Ribo' belonging to the subset 'Ribo'. Further, the feature identification system 102 may facilitate a user to name a subset and assign a color to all the data points starting with 'Ribo' inside the non-linear pattern in a different color.

Figure 3D:
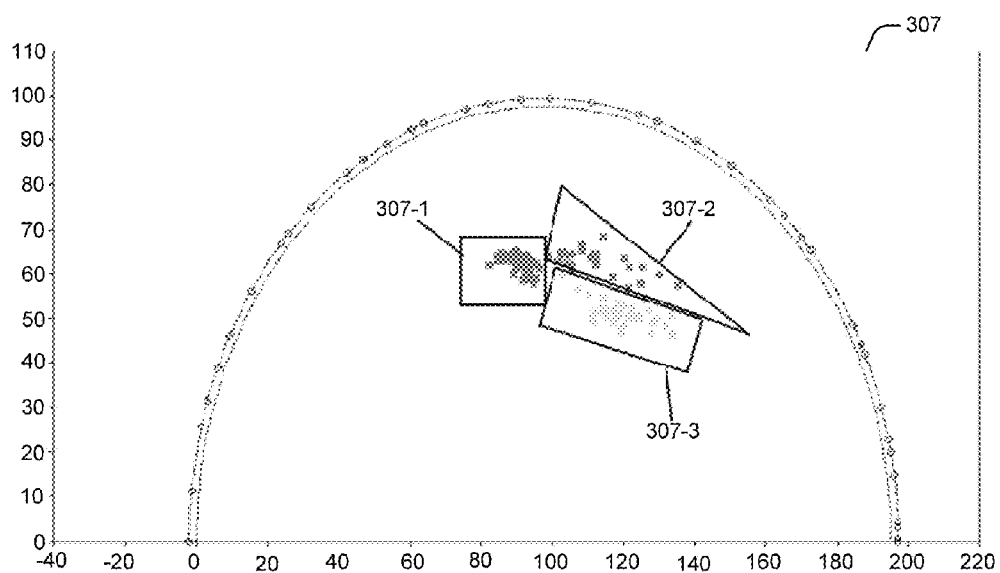
FIG. 3d illustrates a non-linear pattern generated for a plurality of subsets of the first sample data set, in accordance with an embodiment of the present subject matter.

FIG. 3d illustrates a non-linear pattern 307 generated for a plurality of subsets of the first sample data set, in accordance with an embodiment of the present subject matter. It will be understood that the non-linear pattern 307 may be a semi-circle, where each of the features are arranged across the circumference of the semi-circle based on the distances amongst the features. The computation module 120 of the present subject matter may provide separation between the data points belonging to different subsets, such as to the 'Protease', 'Resp', and 'Ribo' subsets. It will be evident that the positioning of the one or more data points may be based on the features placed across the non-linear pattern 307. Accordingly, a clear separation of data points belonging to three different subsets 307-1, 307-2, and 307-3 may be obtained. The feature identification system 102 may therefore effectively resolve the data points based on the features of a subset.

Further, for particular data points, the feature identification system 102 may be configured to generate a heat map. Moreover, a feature variation plot may be generated by using the non-linear pattern 306 by selecting a set of data points. To generate the feature variation plot, the feature identification system 102 may determine an upper limit and a lower limit of features belonging to a subset of the first sample data set as well as a threshold feature value of all the features for the selected data points. Thereafter, the rendering module 122 may generate a threshold non-linear pattern in the two-dimensional plane. The features that may lie above and below the threshold non-linear pattern may be colored differently. This representation may provide a quick idea of the marker features that may be responsible for the variation in the selected subset of data points. The marker features may also be responsible for clustering between the data points of different subsets of the multi-dimensional data.

Figure 3E:
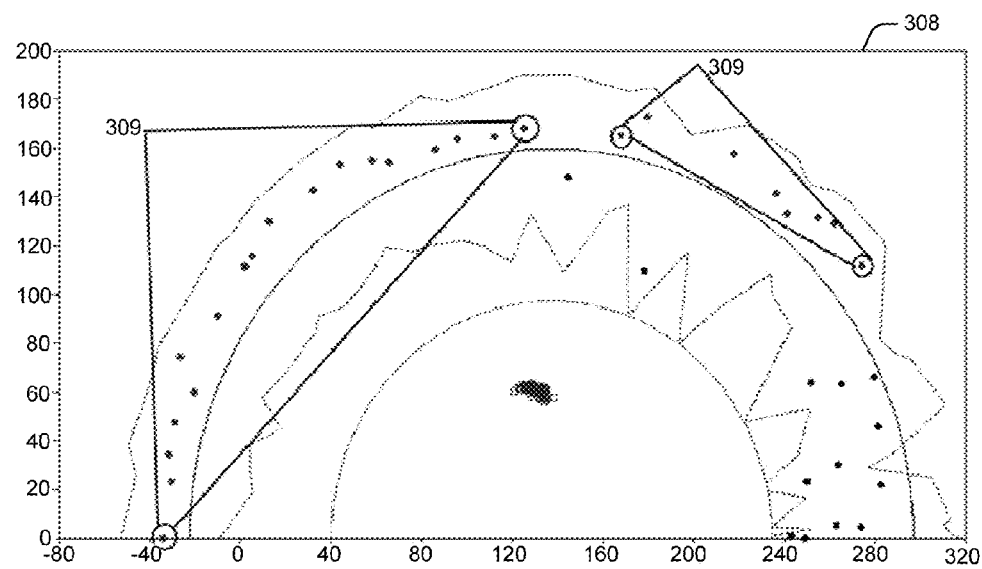
FIGS. 3e to 3g illustrate feature variation plots generated for a plurality of subsets of the first sample data set, in accordance with an embodiment of the present subject matter.
Figure 3F:
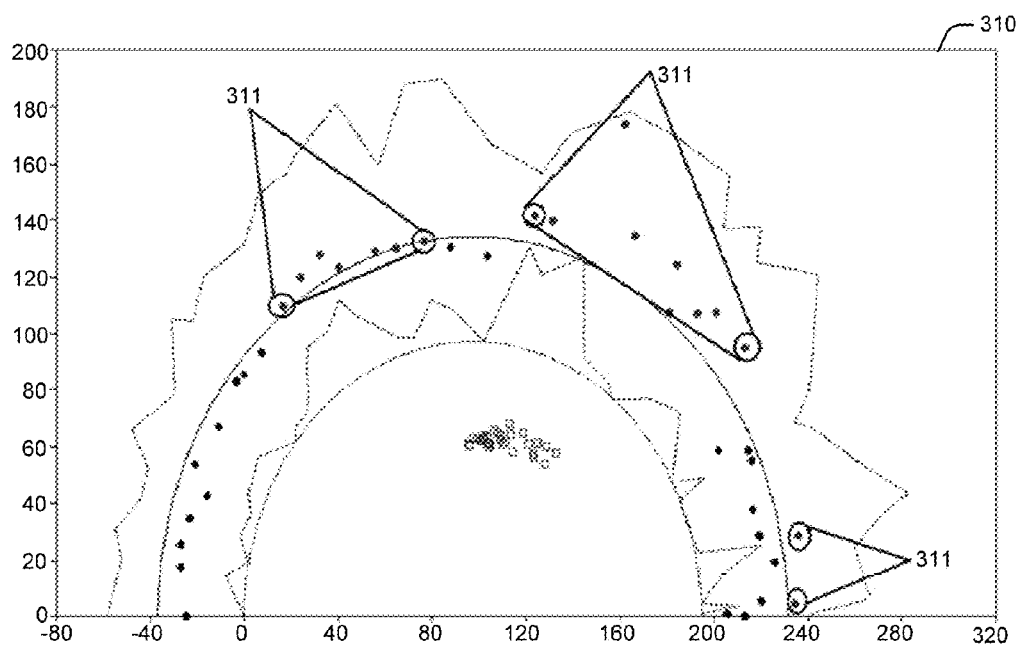
Figure 3G:
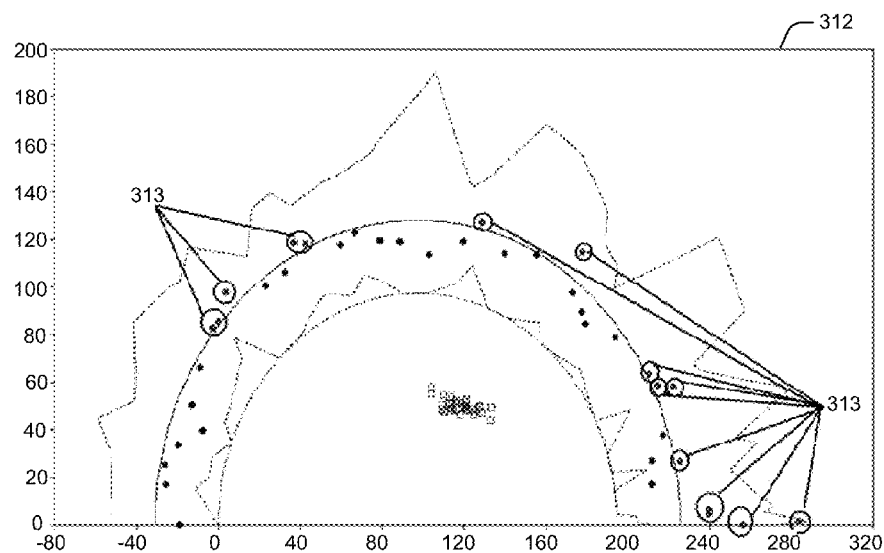

FIGS. 3d to 3f illustrate feature variation plots 308 to 312 generated for a plurality of subsets of the first sample data set, in accordance with an embodiment of the present subject matter. FIG. 3d illustrates an upper limit 307-1, a threshold non-linear pattern 307-2, and a lower limit 307-3 for the 'Ribo' subset of the first sample data set. FIGS. 3d to 3f illustrate that the higher the features are positioned above the threshold non-linear pattern the more is the contribution of the features in the clustering of the data points in the subset. In a similar manner, the feature variation plots 308 to 312 generated for the three subsets, namely, Ribo, Resp, and Proteas are provided in FIGS. 3d to 3f. These figures indicate that each subset is characterized by a combination of several marker features that account for the differential separation of the data points belonging to the respective subsets.

The feature variation plots 308 to 312 may represent that the data points corresponding to the 'Ribo' subset may include a higher expression for a much wider range of features located within the triangular region(s) 309. Therefore, it may be inferred that the 'Ribo' subset is generally expressed under a wide variety of features. On the other hand, as seen in the FIGS. 3e and 3f, the 'Resp' subset, in contrast to the 'Ribo' subset, is seen to have higher expression values only for some specific features located within demarcated triangles 311. Further, the 'Proteas' subset is seen to be characterized by different marker features demarcated individually as 313 as compared to the 'Ribo' and 'Resp' subsets.

In another example of the present subject matter, a second sample data set containing 13 attributes (features) of wine samples, grown in a same region but derived from three different cultivars (subsets) referred to as Wine 1, Wine 2 and Wine 3, is selected. The 13 attributes may include alcohol, malic acid, ash, alkalinity of ash, magnesium, phenols, flavonoids, non-flavanoid phenols, proanthocyanins, color intensity, Hue, OD280/OD315 of diluted wines, and proline. The 13 attributes are numbered from 1 to 13 respectively in the figure for the sake of convenience.

Figure 4A:
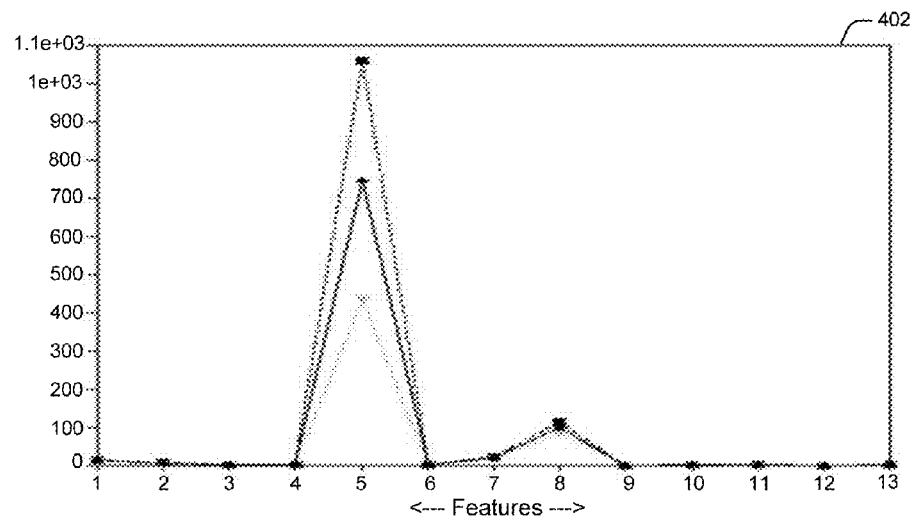
FIG. 4a illustrates variation of feature values across all data points belonging to a second sample data set, in accordance with an embodiment of the present subject matter.

As described with respect to the earlier case study, the computation module 120 of the feature identification system 102 may generate a plot indicating variation in the attributes. FIG. 4a illustrates a plot 402 generated for a second sample data set, in accordance with an embodiment of the present subject matter. The plot 402 displays huge variations in some features of the wine data set as compared to other features. Consequently, the computation module 120 may normalize the feature values associated with each feature of the wine data set. In an implementation, the GUI of the feature identification system 102 may include a tab "Normalize" for normalizing the feature values. The details about normalization of the feature values have been explained in conjunction with FIG. 1 and therefore have not been explained here for the sake of brevity.

Figure 4B:
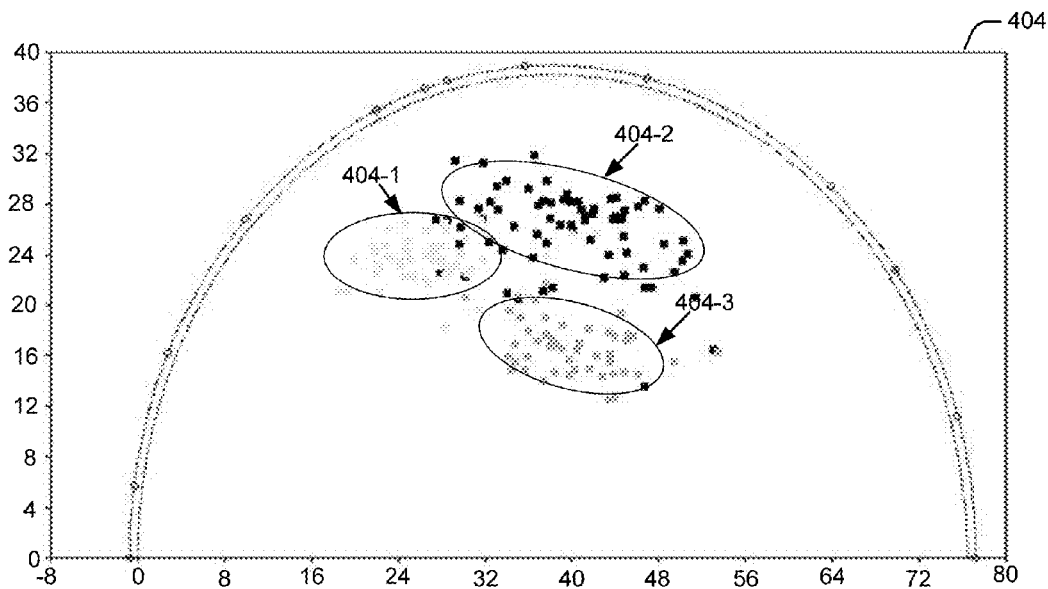
FIG. 4b illustrates a non-linear pattern generated for a plurality of subsets of the second sample data set, in accordance with an embodiment of the present subject matter.

FIG. 4b illustrates a non-linear pattern 404 generated for the second sample data set, such as the wine data set, in accordance with an embodiment of the present subject matter. The non-linear pattern 404 may be generated in a two-dimensional plane for the wine data set. In an implementation, the GUI of the feature identification system 102 may include a button "Plot in Igloo" for generating the non-linear pattern of the features. The non-linear pattern 404 may restrict the data points of the wine data set within the region defined by the non-linear pattern 404. As will be understood that the computation module 120 may use Hooke's Law to evaluate the attractive force exerted on each data point by each of the feature. Based on the evaluation, the computation module 120 may position the data points within the region.

The data points corresponding to the different wine samples may be placed in clusters as indicated in FIG. 4b. Clusters 404-1, 404-2, and 404-3 may indicate the data points belonging to Wine 1, Wine 2, and Wine 3 respectively. Accordingly, the feature identification system 102 may effectively resolve the data points based on the features of a subset.

Figure 4C:
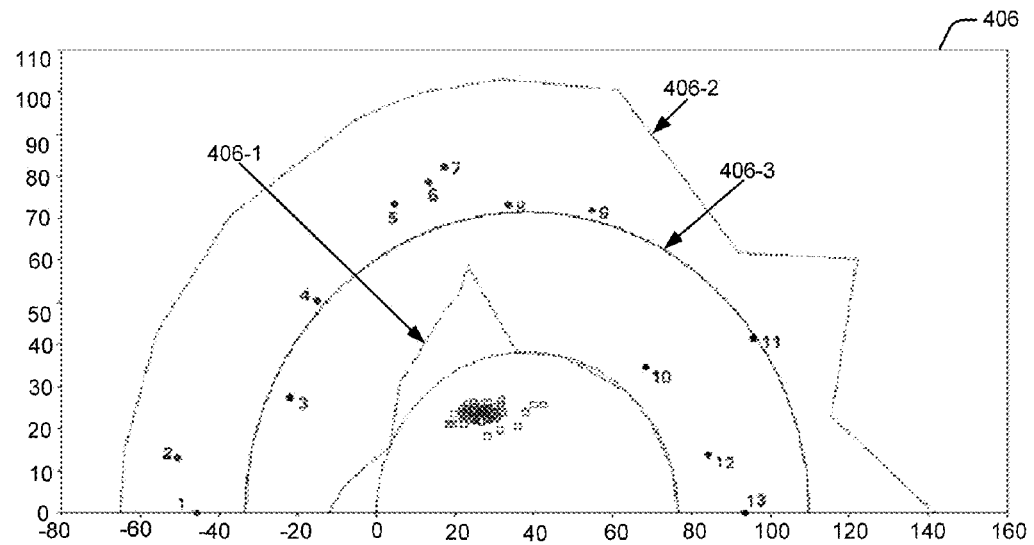
FIGS. 4c to 4e illustrate feature variation plots generated for a plurality of subsets of the second sample data set, in accordance with an embodiment of the present subject matter.
Figure 4D:
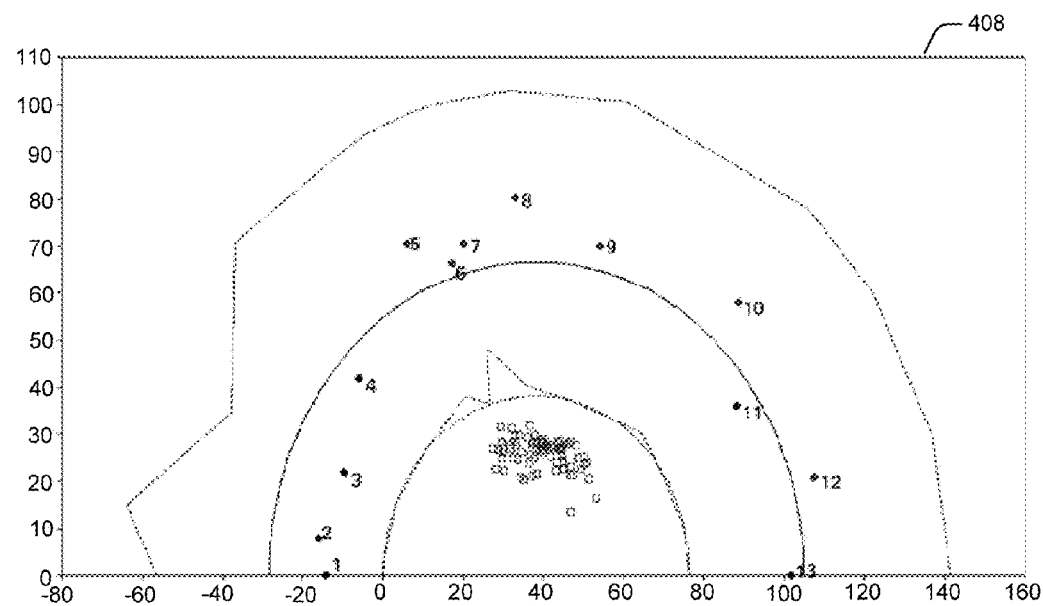
Figure 4E:
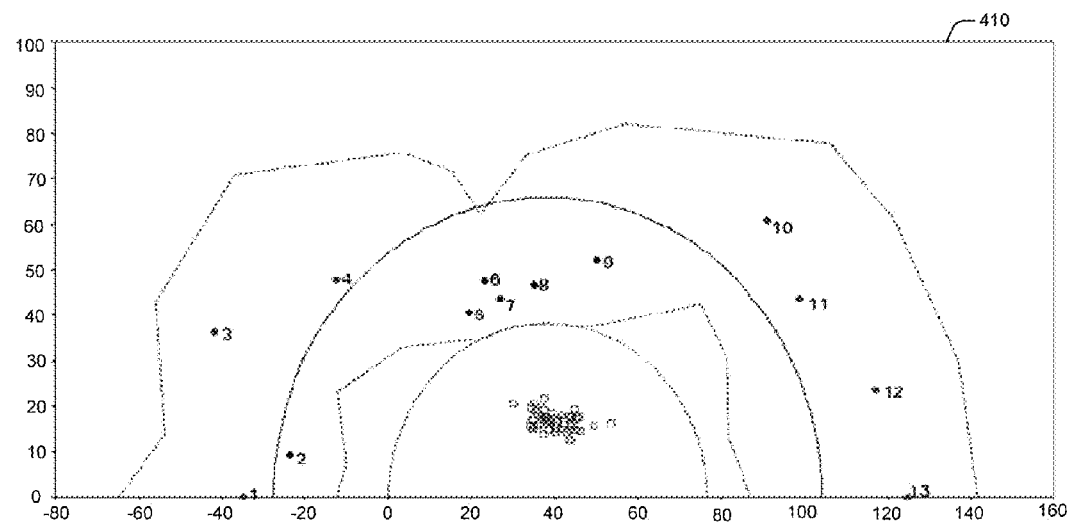
Figure 5A:
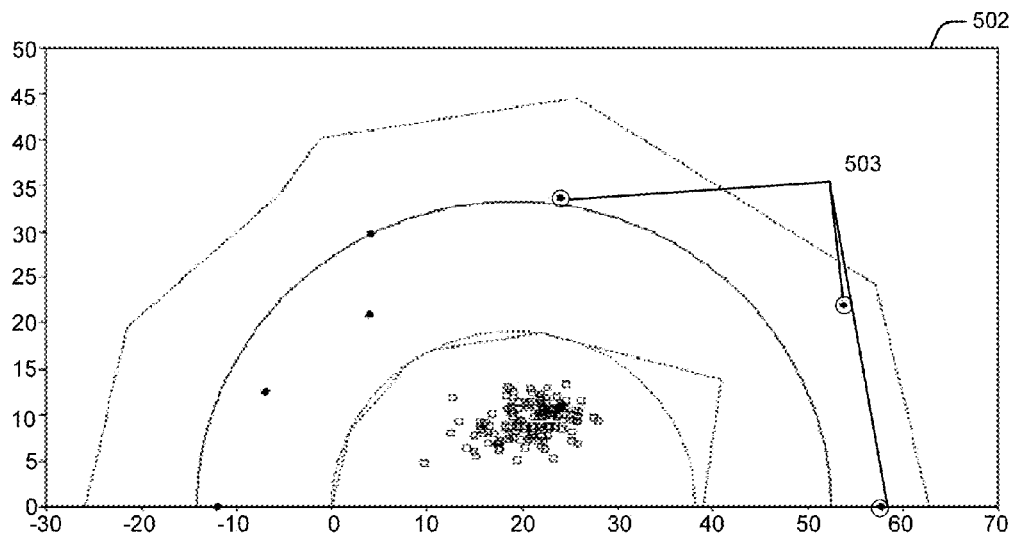
FIGS. 5a to 5d illustrate feature variation plots generated for a plurality of subsets of a third sample data set, in accordance with an embodiment of the present subject matter.
Figure 5B:
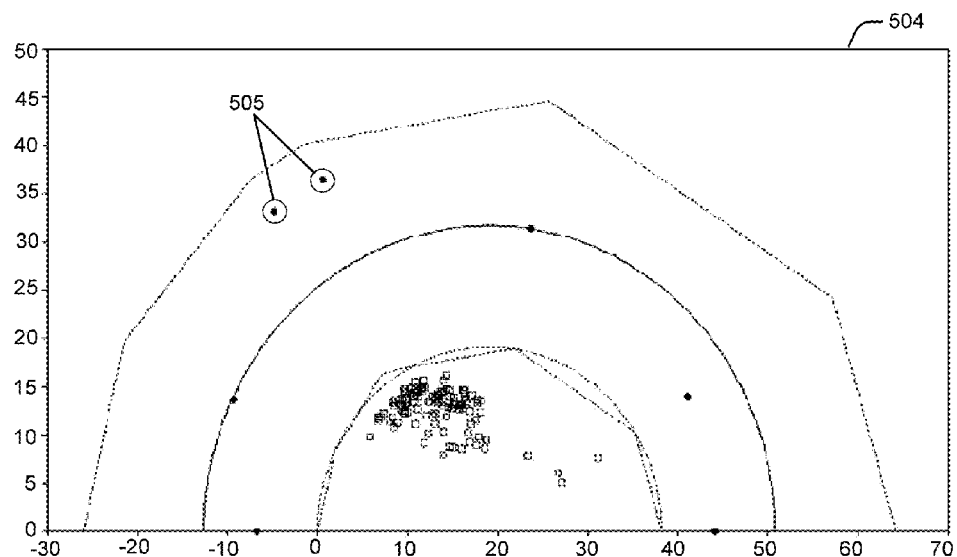
Figure 5C:
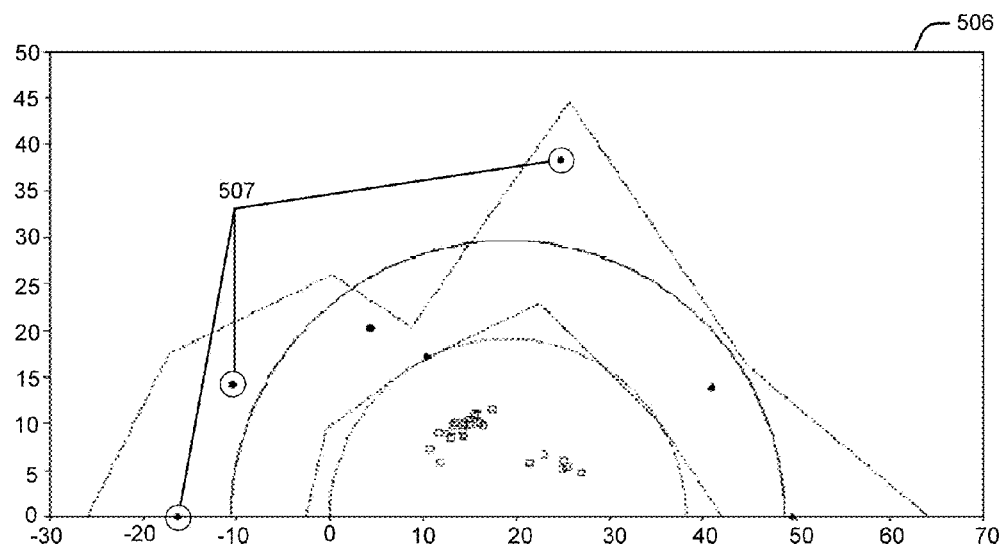
Figure 5D:
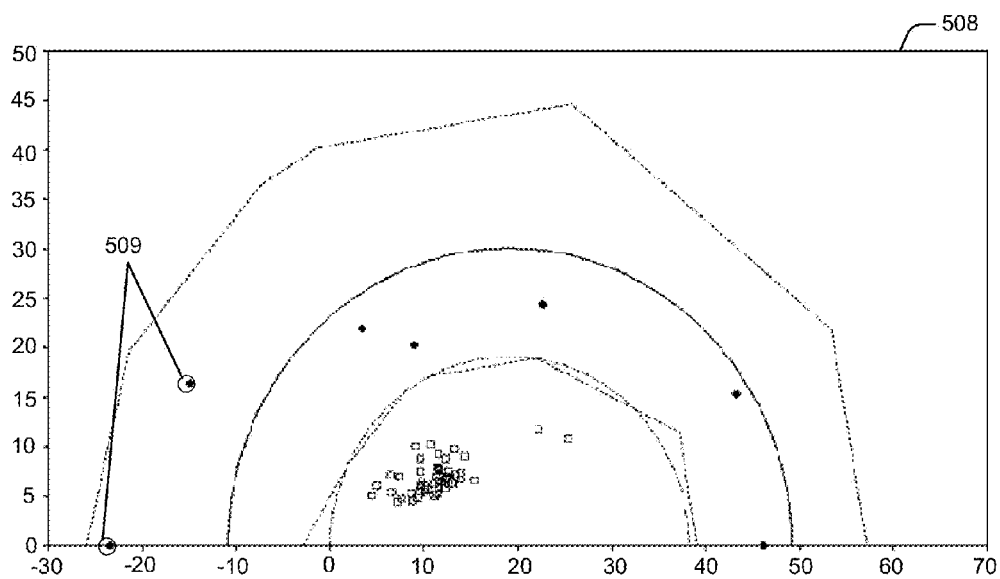

FIGS. 4c to 4e illustrate feature variation plots 406 to 410 generated for a plurality of subsets of the second sample data set, in accordance with an embodiment of the present subject matter. Referring to FIG. 4c, the feature variation plot 406 containing variation in the features of the first wine sample selected from the wine data set is illustrated. FIG. 4d illustrates the feature variation plot 408 containing variation in the features of the second wine sample selected from the wine data set, whereas FIG. 4e illustrates the feature variation plot 410 containing variation in the features of the third wine sample selected from the wine data set. It will be understood that the rendering module 122 of the feature identification system 102 may be configured to generate the feature variation plots. The rendering module 122 may calculate a lower limit 406-1, an upper limit 406-2, and a threshold feature value for the 13 features. Based on the threshold feature value the rendering module 122 may generate a threshold non-linear pattern 406-3 in the two-dimensional plane as illustrated in FIG. 4c.

Accordingly, FIGS. 4c to 4e indicate that the three subsets of the wine data set are characterized by different combinations of the features. Differently plotting the feature variations may identify characteristic or marker features, of each subset, that account for differential clustering of the three subsets of the wine data set. This indicates that the subsets Wine 1 and Wine 2 show an almost similar pattern for features namely, 5, 6, 7, 8, 9. However, while Wine 1 is characterized by a higher abundance of feature 1 and 2 with a lower abundance in feature 10 and 12, Wine 2 is characterized by an exact opposite pattern of feature abundance where in feature 1 and 2 are in lower abundance while 10 and 12 are in higher abundance. Further, Wine 3 is observed to possess a distinct pattern of feature variations as compared to the other two Wine subsets with a distinct higher abundance of marker features 3, 10, 11, 12, 13 and a lower abundance of features 5, 6, 7, 8, 9 (which was high in both Wine 1 and Wine 2).

In yet another example, protein sequence data set was considered as a third sample data set. The protein sequence data set includes feature values of seven different features of protein sequences of E. coli. These features may include McGeoch's method for signal sequence recognition (mcg), von Heijne's method for signal sequence recognition (gvh), von Heijne's Signal Peptidase II consensus sequence score (lip), presence of charge on N-terminus of predicted lipoproteins (chg), score of discriminant analysis of the amino acid content of outer membrane and periplasmic proteins (aac), score of the ALOM membrane spanning region prediction program (alm1), and score of ALOM program after excluding putative cleavable signal regions from the sequence (alm2). For the sake of convenience the features are marked 1 to 7 respectively in the figure.

Further, the protein sequence data set may be divided into four major subsets based on localization site of these protein sequences. The four subsets that may be formed from the protein sequence data set may be cytoplasm, inner membrane, outer membrane, and periplasm.

The feature identification system 102 may facilitate in generation of a plot as described above. In the present case, the plot indicates an uneven distribution of the feature values across the seven features of the protein sequence data set. Accordingly, the computation module 120 may normalize the feature values and compute correlation distances between the features in each of the feature pairs of the protein sequence data set. Thereafter, distance between each feature may be represented on linear coordinates. Consequently, the linear coordinates may be geometrically transformed into non-linear coordinates, i.e., in a semi-circular pattern. The features may be arranged across the circumference of the semi-circle based on the relative distance between each of the features.

FIGS. 5a to 5d illustrate feature variation plots 502 to 508 generated for a plurality of subsets of a third sample data set, in accordance with an embodiment of the present subject matter. As described above, the rendering module 122 may represent the lower limit, upper limit, and the threshold non-linear pattern for each of the subsets. The features variations with respect to each of the subsets may be identified efficiently by the feature identification system 102. The marker features, demarcated as 503, 505, 507, and 509, that may responsible for clustering of the data points of each of the respective subsets may be determined easily.

In still another example, a fourth sample data set may be considered. The fourth sample data set may include 800 genes. The 800 genes were classified into several subsets based on correlation between genes. In the present example, genes from G1 and S/G2 subsets were used. In this data set, the genes may be referred as a set of data points and gene expressions at the different time points may be referred as a set of features/attributes.

Figure 6A:
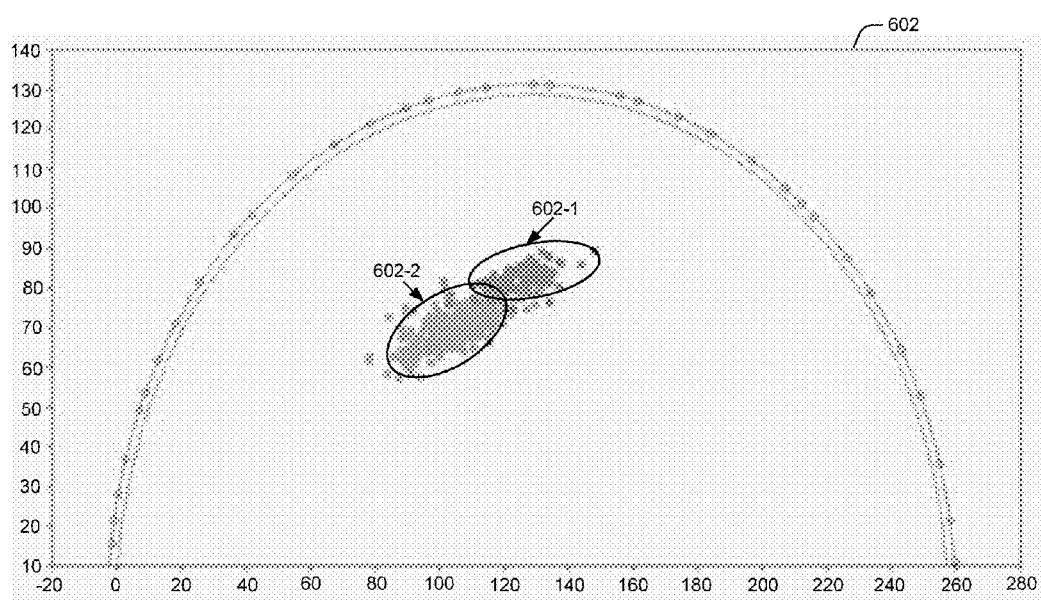
FIG. 6a illustrates a non-linear pattern generated for a plurality of subsets of a fourth sample data set, in accordance with an embodiment of the present subject matter.

FIG. 6a illustrates a non-linear pattern 602 generated for a plurality of subsets of a fourth sample data set, in accordance with an embodiment of the present subject matter. The feature identification system 102 may generate the non-linear pattern 602 for the set of features across the set of data points. It will be understood that the non-linear pattern 602 may be a semi-circle, where each of the features are arranged across the circumference of the semi-circle based on the distances amongst the features. As explained in conjunction with above case studies, the computation module 120 may position the one or more data points within the non-linear pattern 602. It will be evident that the positioning of the one or more data points may be based on the features places across the non-linear pattern 602. The one or more data points may therefore be clustered as 602-1 and 602-2.

Figure 6B:
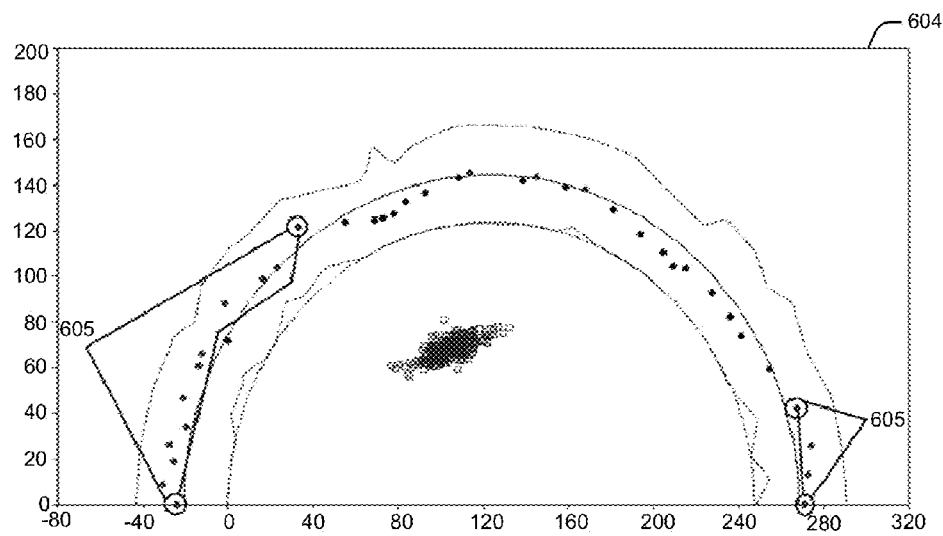
FIGS. 6b and 6c illustrate feature variation plots generated for each of the plurality of subsets of the fourth sample data set, in accordance with an embodiment of the present subject matter.
Figure 6C:
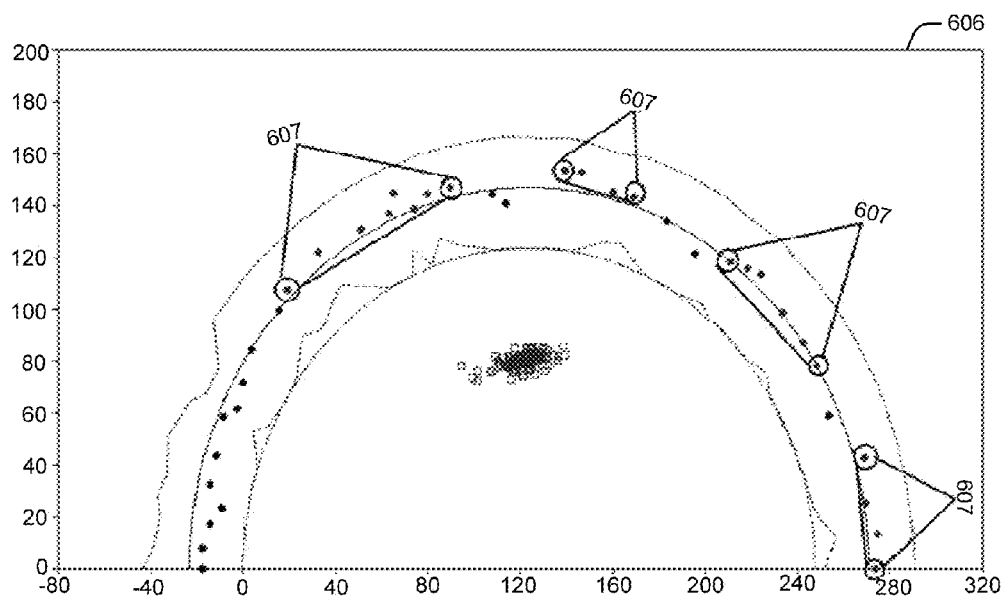

The rendering module 122 may facilitate generation of feature variation plots 604 and 606 as depicted in FIGS. 6b and 6c. FIGS. 6b and 6c illustrate feature variation plots 604 and 606 generated for a plurality of subsets of the fourth sample data set, in accordance with an embodiment of the present subject matter. FIGS. 6b and 6c reflect that the genes corresponding to the G1 and those belonging to the S/G2 subsets have clustered distinctly from each other. Furthermore, the feature variation plots 604 and 606 may clearly identify a distinct set of features obtained from these two subsets.

As described with conjunction of the above example, the feature identification system 102 may facilitate in generating an upper limit, a lower limit, and a threshold non-linear pattern in the two-dimensional plane (as seen in FIGS. 6b and 6c). This may enable to extract inferences from the feature variation plots 604 and 606. For example, the features demarcated by the regions 605 and 607 depict the marker features for the G1 and S/G2 phases depicted in feature variation plots 604 and 606 respectively. A careful observation of the two feature variation plots 604 and 606 may indicate that many of the features that are abundant in G1 phase are in lower abundance in S/G2 phase. On the other hand, some of the features which are abundant in S/G2 phase are observed to be in low abundance in G1 phase. Accordingly, the non-linear pattern of the features may not only resolve the data points based on their constituent features but may also identify features that may be responsible for these variations.

We claim:

1. A method for identifying marker features of one or more subsets of a multi-dimensional data, each of the one or more subsets including a plurality of data points associated with a plurality of features, wherein each of the plurality of data points is defined by feature values corresponding to the associated features, the method comprising:
   identifying, by a processor, a plurality of feature pairs based on a matrix of the plurality of data points and the plurality of features;
   computing, by the processor, correlation distances between features in each of the plurality of feature pairs based on correlation co-efficient values, wherein a lower correlation distance between the features indicate a highly related feature pair;
   generating, by the processor, a semi-circle of the plurality of features from a linear pattern of the plurality of features, in a two-dimensional plane, based on the correlation distances, such that the features in the highly related feature pair are placed closer to each other than the features not highly related to each other;
   evaluating, by the processor, force exerted on each of the plurality of data points by each of the plurality of features and positioning each of the plurality of data points within a region defined by the semi-circle in the two-dimensional plane, based on the evaluation;
   calculating, by the processor, a mean feature value for each of the features of the plurality of data points of a particular subset from amongst the one or more subsets, wherein based on the calculating, identifying an overall mean of the mean values associated with each of the plurality of features across each of the plurality of data points;
   representing, by the processor, the overall mean feature value as another semi-circle in the two-dimensional plane and with respect to the overall mean feature value, representing the mean values of each of the features corresponding to the plurality of data points in the particular subset in the two-dimensional plane, wherein the representing comprises identifying a lower bound and an upper bound corresponding to each feature for the particular subset for being plotted in the another semi-circle in the two dimensional plane; and
   determining, by the processor, the marker features based on a relative position of the mean feature values with respect to the overall mean feature value in the two-dimensional plane, wherein the marker features distinguish a first subset of the multi-dimensional data from a second subset thereof.

2. The method as claimed in claim 1, wherein the computing the correlation distances further comprises determining a variation of the feature values across the plurality of data points and normalizing the feature values based on the determination of the variation.

3. The method as claimed in claim 1, wherein the generating the semi-circle pattern further comprises arranging the plurality of features in a linear pattern based on the correlation distances computed between each of the plurality of features.

4. The method as claimed in claim 3, wherein the arranging comprises:
   flagging each of the plurality of features;
   defining a cut-off value based on the correlation distances between the features in each of the plurality of feature pairs;
   creating a plurality of groups of flagged features based on selection of a primary feature from each of the plurality of features, wherein the plurality of groups include a set of features lying at a distance equal to and less than the cut-off value from the primary feature of respective groups, and wherein each of the plurality of groups include a unique set of flagged features;
   storing the cut-off value and number of the plurality of groups obtained at the cut-off distance;
   incrementing the cut-off value and creating the plurality of groups unless only one group including all features is created; and
   aligning each of the flagged feature in the linear pattern based on the stored cut-off value and respective number of the plurality of groups.

5. The method as claimed in claim 1, wherein the generating the semi-circle pattern further comprises evaluating force exerted on each of the plurality of data points by each of the plurality of features and positioning each of the plurality of data points within a region defined by the semi-circle, in the two-dimensional plane, based on the evaluation.

6. The method as claimed in claim 1 further comprising reducing dimensionality of the multi-dimensional data by using one of an evaluation plot technique and a correlation filtering technique.

7. The method as claimed in claim 1 further comprising providing variations in features associated with the one or more subsets upon comparison of the one or more subsets, wherein the variations are determined based on the mean feature value calculated for the subset.

8. The method as claimed in claim 1, wherein the determining the marker features comprises identifying the relative position of the mean feature values for the subset positioned away from the overall mean of mean of the feature values associated with each of the plurality of features across each of the plurality of data points as the another semi-circle in the two-dimensional plane.

9. A feature identification system for identifying marker features of one or more subsets of a multi-dimensional data, each subset including a plurality of data points associated with a plurality of features, wherein each of the plurality of data points defined by feature values corresponding to the associated features, the feature identification system comprising:
    a processor;
    an interface; and
    a memory coupled to the processor, the memory comprising:
        a computation module configured to,
            identify a plurality of feature pairs based on a matrix between the plurality of data points and the plurality of features;
            compute correlation distances between features in each of the plurality of feature pairs based on correlation co-efficient values, wherein a lower correlation distance between features indicate a highly related feature pair; and
            generate a semi-circle pattern of the plurality of features from a linear pattern of the plurality of features, in a two-dimensional plane, based on the correlation distances, such that the features in the highly related feature pair are placed close to each other than the features not highly related to each other;
            evaluate force exerted on each of the plurality of data points by the each of the plurality of features and position of each of the plurality of data points within a region defined by the semi-circle, in the two-dimensional plane, based on the evaluation; and
        a rendering module configured to,
            calculate a mean feature value for each of the associated features of the data points of a particular subset from amongst the one or more subsets, wherein based on the calculation, an overall mean of the mean values associated with each of the plurality of features across each of the plurality of data points is identified;
            represent the overall mean feature value as another semi-circle in the two-dimensional plane and with respect to the overall mean feature value, represent the mean values of each of the features corresponding to the data points in the particular subset in the two-dimensional plane, wherein the representing comprises identifying a lower bound and an upper bound corresponding to each feature for the particular subset for being plotted in the another semi-circle in the two dimensional plane; and
            determine the marker features based on a relative position of the mean feature values with respect to the overall mean feature value in the two-dimensional plane, wherein the marker features distinguish a first subset of the multi-dimensional data from a second subset thereof.

10. The feature identification system as claimed in claim 9, wherein the computation module is further configured to determine a variation of the feature values across the data points and normalize the feature values based on the determination.

11. The feature identification system as claimed in claim 9, wherein the computation module is further configured to arrange the plurality of features in a linear pattern based on the correlation distances computed between each of the plurality of features, the arrangement comprises:
    flag each of the plurality of features;
    define a cut-off value based on the correlation distances between the features in each of the plurality of feature pairs;
    create a plurality of groups of flagged features based on selection of a primary feature from each of the plurality of features, wherein the plurality of groups include a set of features lying at a distance equal to and less than the cut-off value from the primary feature of respective groups, and wherein each of the plurality of groups include a unique set of flagged features;
    store the cut-off value and number of the plurality of groups obtained at the cut-off value;
    increment the cut-off value and create the plurality of groups until only one group including all features is created; and
    align each of the flagged feature in the linear pattern based on the stored cut-off value and respective number of the plurality of groups.

12. The feature identification system as claimed in claim 9, wherein the rendering module is further configured to provide variations in features associated with the one or more subsets upon comparison of the one or more subsets, wherein the variations are determined based on the mean feature value calculated for the subset.

13. The feature identification system as claimed in claim 9, wherein the rendering module is configured to determine the marker features by identifying the relative position of the mean feature values for the subset positioned away from the overall mean of mean of the feature values associated with each of the plurality of features across each of the plurality of data points as the another semi-circle in the two-dimensional plane.

14. A non-transitory computer-readable medium having embodied thereon a computer program for executing a method for identifying marker features of one or more subsets of a multi-dimensional data, each subset including a plurality of data points associated with a plurality of features, wherein each of the plurality of data points is defined by feature values corresponding to the associated features, the method comprising:
    identifying a plurality of feature pairs based on a matrix of the plurality of data points and the plurality of features;
    computing correlation distances between features in each of the plurality of feature pairs based on correlation co-efficient values, wherein a lower correlation distance between the features indicate a highly related feature pair;

generating a semi-circle of the plurality of features from a linear pattern of the plurality of features, in a two-dimensional plane, based on the correlation distances, such that the features in the highly related feature pair are placed closer to each other than the features not highly related to each other;

evaluating, by the processor, force exerted on each of the plurality of data points by each of the plurality of features and positioning each of the plurality of data points within a region defined by the semi-circle in the two-dimensional plane, based on the evaluation;

calculating a mean feature value for each of the associated features of the data points of a particular subset from amongst the one or more subsets, wherein based on the calculating, identifying an overall mean of the mean values associated with each of the plurality of features across each of the plurality of data points;

representing the overall mean feature value as another semi-circle in the two-dimensional plane and with respect to the overall mean feature value, representing the mean values of each of the features corresponding to the data points in the particular subset in the two-dimensional plane, wherein the representing comprises identifying a lower bound and an upper bound corresponding to each feature for the particular sub-set for being plotted in the another semi-circle in the two dimensional plane; and determining the marker features based on a relative position of the mean features values with respect to the overall mean feature value in the two-dimensional plane, wherein the marker features distinguish a first subset of the multi-dimensional data from a second subset thereof.

* * * * *